(12) United States Patent
Anderson et al.

(10) Patent No.: US 7,667,058 B2
(45) Date of Patent: Feb. 23, 2010

(54) HYDROGENATION PROCESS

(75) Inventors: Kris Anderson, Belfast (GB); Peter Goodrich, Belfast (GB); Christopher Hardacre, Belfast (GB); Sarah Elizabeth Jane McMath, Moria (GB)

(73) Assignee: The Queen's University of Belfast, Belfast (GB)

( * ) Notice: Subject to any disclaimer, the term of this patent is extended or adjusted under 35 U.S.C. 154(b) by 749 days.

(21) Appl. No.: 10/478,039

(22) PCT Filed: May 17, 2002

(86) PCT No.: PCT/GB02/02333

§ 371 (c)(1),
(2), (4) Date: Jul. 30, 2004

(87) PCT Pub. No.: WO02/094740

PCT Pub. Date: Nov. 28, 2002

(65) Prior Publication Data

US 2004/0267034 A1 Dec. 30, 2004

(30) Foreign Application Priority Data

May 18, 2001 (GB) .................................. 0112093.0

(51) Int. Cl.
*C07C 51/36* (2006.01)
(52) U.S. Cl. ........................ 554/141; 564/489; 568/880; 585/259

(58) Field of Classification Search ....................... None
See application file for complete search history.

(56) References Cited

U.S. PATENT DOCUMENTS 5,490,919 A 2/1996 Pri-Bar et al.
6,040,263 A 3/2000 Mussmann et al.

OTHER PUBLICATIONS

Carlin et al.,Chemical Communications, 1997.*
Carlin et al., Electrochemical Society, 2000.*
Holderich et al., Royal Society of Hemistry, 2001.*
Carlin, Richard T. et al, "Ionic Liquid-Polymer Gel Catalytic Membrane", Chemical Communications (Cambridge) 1997.
Carlin, Richard T. et al, "Heterogeneous Catalytic Hydrogenation With Supported Ionic Liquid Membranes", Proceedings—Electrochemical Society 2000.
Holderich, Wolfgang F. et al. "Immobilized Catalysts and Their Use In The Synthesis Of Fine And Intermediate Chemicals", Special Publication—Royal Society of Chemistry 2001.

(Continued)

*Primary Examiner*—Deborah D Carr
(74) *Attorney, Agent, or Firm*—Hodgson Russ LLP

(57) ABSTRACT

Disclosed are heterogeneous processes (i) for the hydrogenation of a compound containing at least one unsaturated carbon-carbon bond, and (ii) for the hydro-dehalogenation of a compound containing at least one C—Cl, C—Br or C—I bond. The processes comprise reacting said compound with a hydrogenating agent and a heterogeneous hydrogenation catalyst in the presence of an ionic liquid.

35 Claims, 13 Drawing Sheets

OTHER PUBLICATIONS

Figure 1A:
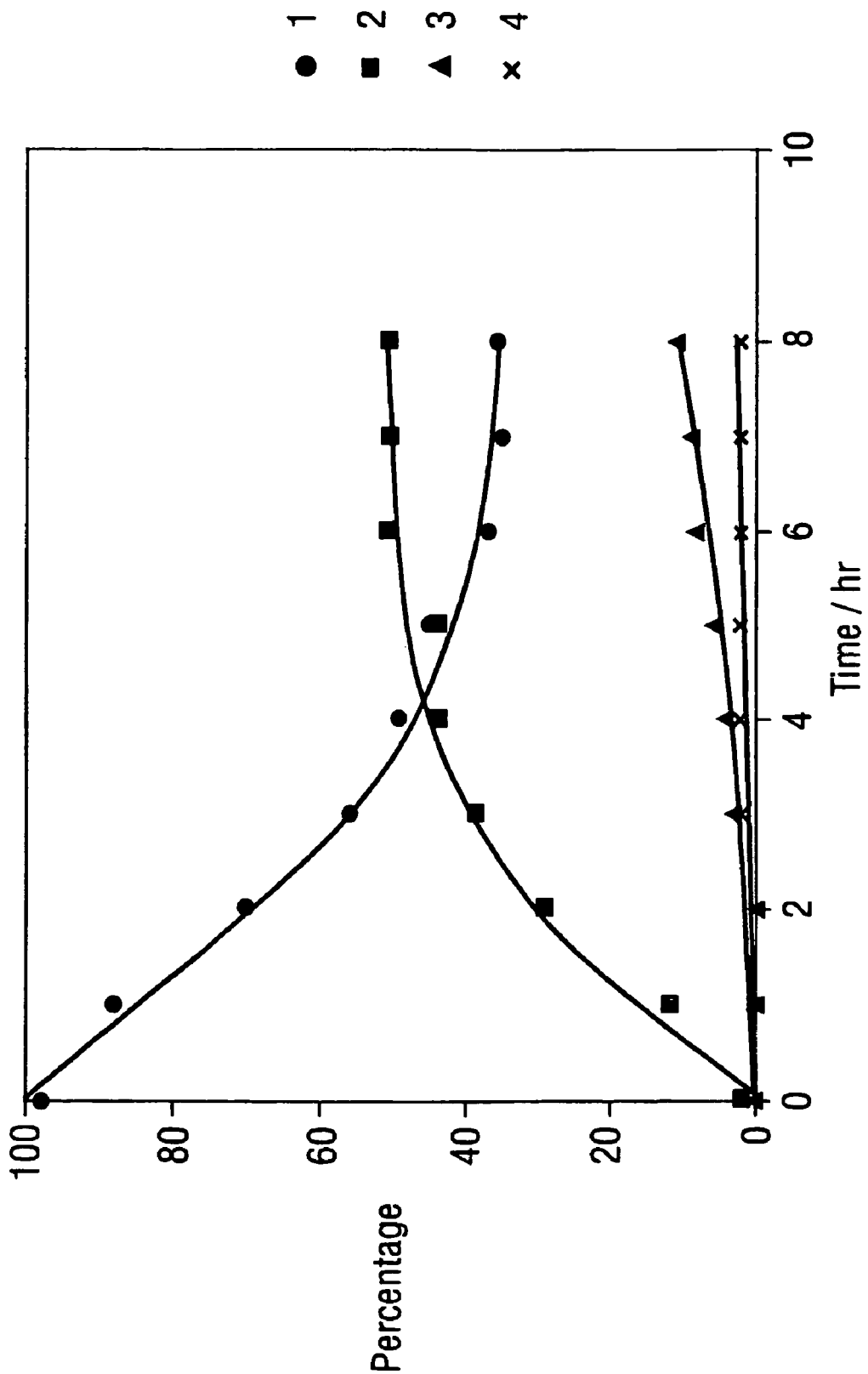

Dupont, Jairton et al, "Transition—Metal Nanoparticles In Imidazolium Ionic Liquids: Recycable Catalysts For Biphasic Hydrogenation Reactions", Journal Of The Americal Chemical Society 2002.

Suarez, Paulo A.Z. et al, Two-Phase Catalytic Hydrogenation Of Olefins by Ru(II) and Co(II) Complexes Dissolved In I-N-Butyl-3-Methylimidasolium Tetrafluoroborate Ionic Liquid, Inorganica Chimica Acta 255 1997.

Oliver, Helene et al, "Nonaqueous Room-Temperature Ionic Liquids: A New Class Of Solvents For Catalytic Organic Reactions", Chem. Ind. (Dekker) 1996.

Nippon Kagakukai (Japanese Chemical Society), vol. 4, Jitsuken Kagaku Koza (Experimental Chemical Lecture) 26 Yukikagakugosei VIII, "Asymmetric Synthesis Reduction Sugar Labeled Compound," Maruzen Co., 1992, pp. 253-263.

* cited by examiner

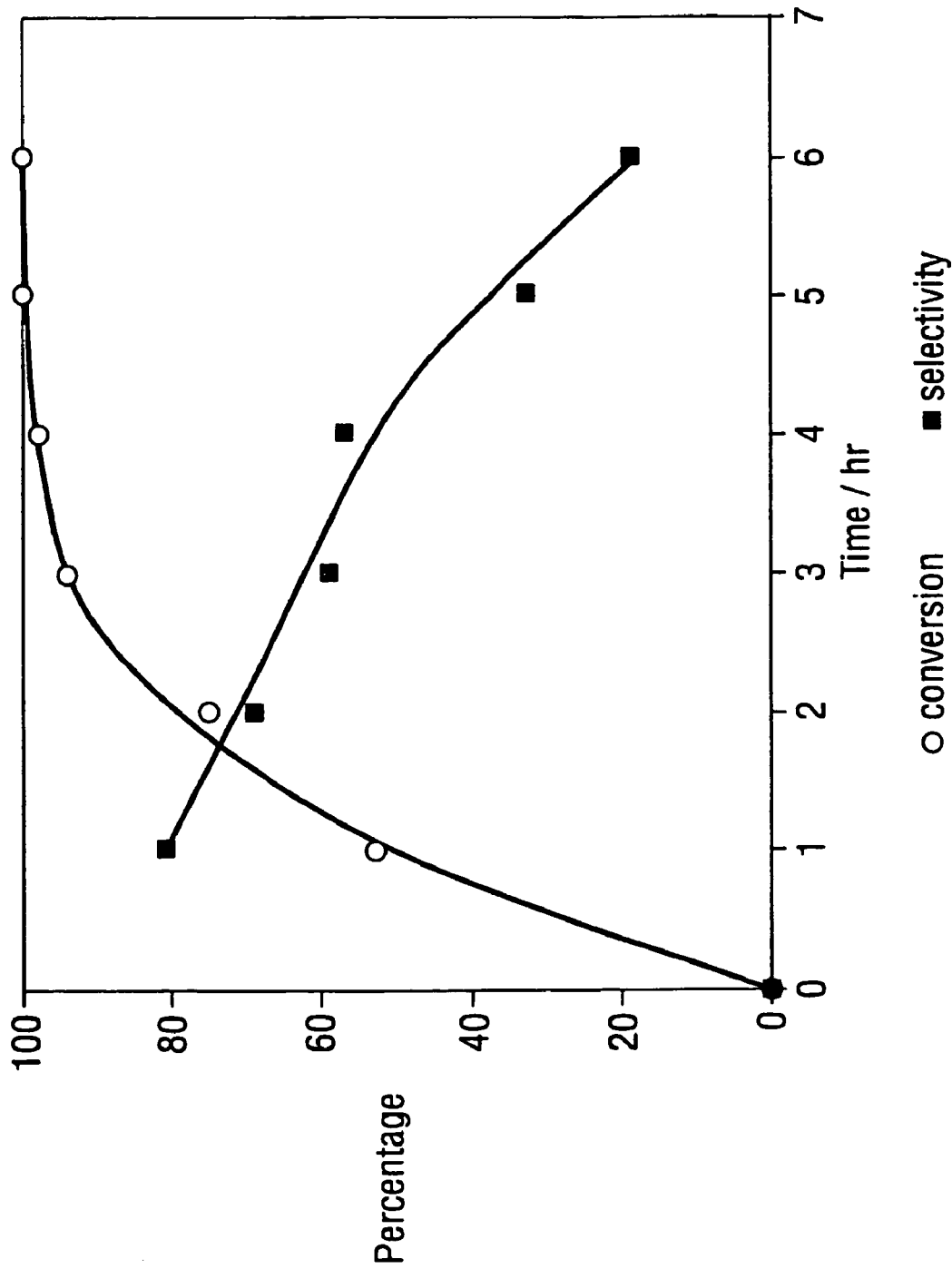

HYDROGENATION PROCESS

This invention relates to hydrogenation processes, and their products. As used herein, the term "hydrogenation" also includes hydro-dehalogenation.

Hitherto, hydrogenation reactions have been carried out in organic solvents such as propan-2-ol. However, such solvents often need promoters to be selective and it is still necessary to extract the reaction product(s) from the solvent.

The present invention aims to overcome these disadvantages and further, provides novel processes that allow hydrogenation reactions to be performed with better selectivities than hitherto.

According to one aspect of the present invention, there is provided a process for the catalytic hydrogenation of a compound containing at least one unsaturated carbon-carbon bond, said process comprising reacting said compound with a hydrogenating agent and a heterogeneous hydrogenation catalyst in the presence of an ionic liquid.

The invention further provides a process for the hydro-dehalogenation of a compound containing at least one C—Cl, C—Br or C—I bond, the process comprising reacting said compound with a hydrogenating agent and a heterogeneous hydrogenation catalyst in the presence of an ionic liquid. Thus, the present invention includes a heterogeneous process for the hydro-dechlorination of a compound, wherein a compound containing at least one C—Cl bond, and a hydrogenation agent are admixed in the presence of an ionic liquid.

The invention may thus be defined in its first aspect as a heterogeneous process for the hydrogenation of unsaturated aliphatic carbons in a compound, wherein the compound and a hydrogenating agent are admixed in the presence of an ionic liquid.

More than one ionic liquid or any combination of ionic liquids may be used in the present invention.

The term "ionic liquid" refers to a liquid that is capable of being produced by melting a solid, and when so produced, consists solely of ions. Ionic liquids may be derived from organic salts, especially salts of heterocyclic nitrogen-containing compounds, and such ionic liquids are particularly preferred for use in the processes of the present invention.

An ionic liquid may be formed from a homogeneous substance comprising one species of cation and one species of anion, or can be composed of more than one species of cation and/or anion. Thus, an ionic liquid may be composed of more than one species of cation and one species of anion. An ionic liquid may further be composed of one species of cation, and one or more species of anion.

Thus, in summary, the term "ionic liquid" as used herein may refer to a homogeneous composition consisting of a single salt (one cationic species and one anionic species) or it may refer to a heterogeneous composition containing more than one species of cation and/or more than one species of anion.

The term "ionic liquid" includes compounds having both high melting temperature and compounds having low melting points, e.g. at or below room temperature (i.e. 15-30° C.). The latter are often referred to as "room temperature ionic liquids" and are usually derived from organic salts having pyridinium and imidazolium-based cations.

A feature of ionic liquids is that they have particularly low (essentially zero) vapour pressures. Many organic ionic liquids have low melting points (e.g. less than 100° C., particularly less than 100° C., and around room temperature, e.g. 15-30° C. Some have melting points well below 0° C.

Ionic liquids may be regarded as consisting of two components, which are a positively charged cation and a negatively charged anion. Generally, any compound that meets the criteria of being a salt (consisting of an anion and cation) and which is fluid at or near the reaction temperature, or exists in a fluid state during any stage of the reaction can be defined as an ionic liquid especially suitable for use in the process of the present invention.

For example, suitable ionic liquids for use in the present invention include salts of alkylated or polyalkylated heteroaryl compounds, such as salts of alkylated pyridine, pyridazine, pyrimidine, pyrazine, imidazole, pyrazole, oxazole and triazole. Thus, examples of suitable ionic liquids include those having the following formula:

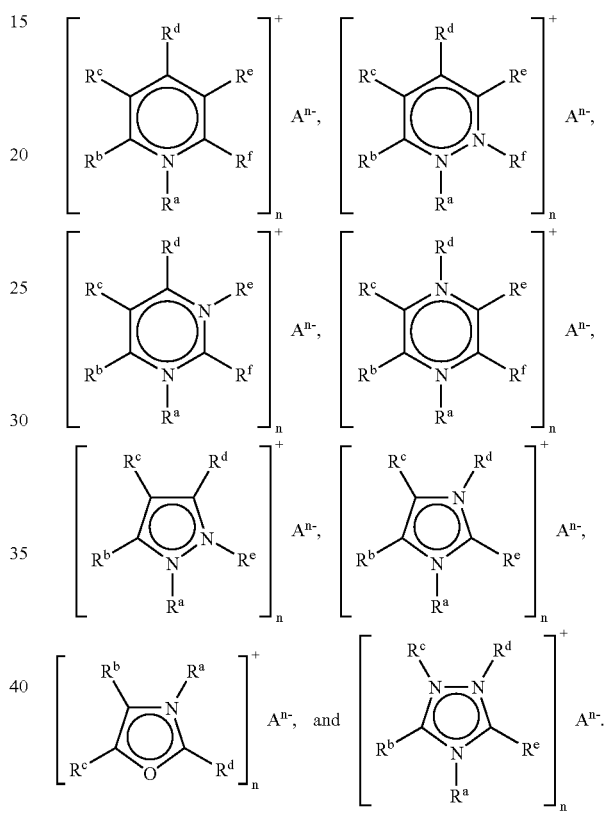

wherein $R^a$ is a $C_1$ to $C_{40}$ (preferably $C_1$ to $C_{20}$ and more preferably $C_4$ to $C_{12}$) straight chain or branched alkyl group or a $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;

$R^b$, $R^c$, $R^d$, $R^e$ and $R^f$ can be the same or different and are each independently selected from H or any of the $R^a$ groups as defined above; and A represents an anion having a charge n–; wherein n may be 1-3. Preferably, in the above compounds, n is 1.

Preferably, $R^a$ is an unsubstituted alkyl or cycloalkyl group as defined above. $R^b$, $R^c$, $R^d$, $R^e$ and $R^f$ are preferably hydrogen.

In preferred ionic liquids for use in the processes of the present invention, the cation is preferably 1,3-dialkylimidazolium. Other cations for this process include other substituted pyridinium or alkyl- or poly-alkylpyridinium, alkyl imidazolium, imidazole, alkyl or poly-alkylimidazolium, alkyl or polyalkylpyrazolium, ammonium, alkyl or polyalkyl ammonium, alkyl or poly-alkyl phosphonium cations.

The anion for the present processes is preferably a phosphate or amide. Other anions include sulfur-containing anions such as sulfate or sulphite, nitrogen-containing anions, such as nitrate, nitrite, alkylsulfate, or a chloride, bromide or other halide, hydrogensulfate, oxoanions of metals, selenium, tellurium, phosphorus, arsenic, antimony, bismuth based anions, and boron halide anions, such as tetrafluoroborate, [$BF_4$].

Particularly preferred ionic liquids are imidazolium, pyridinium or pyrazolium salts. Thus, ionic liquids useful for the process of the present invention include those based on imidazolium cations having the formula:

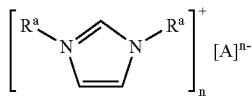

wherein
each $R^a$ may be the same or different and each is independently selected from $C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;
A represents one or more species of anion having charge n−; and
n represents 1-3.

Also suitable for the processes of the present invention are ionic liquids based on pyridinium cations having the formula:

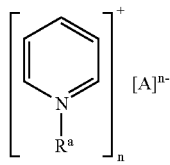

wherein
$R^a$ is selected from $C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;
A represents one or more species of anion having charge n−; and
n represents 1-3.

Preferably, in the above ionic liquids, $R^a$ is independently selected from $C_1$ to $C_{40}$, preferably $C_1$ to $C_{20}$, and even more preferably, $C_4$ to $C_{12}$, straight chain or branched alkyl.

Preferred ionic liquids include those of the above formulae wherein A represents a single species of anion having charge n−; anions having a charge of 1 are especially preferred.

Ionic liquids useful in the present processes include those wherein A represents an anion selected from boron or phosphorus fluorides, $NO_3$, $SO_4$, $HSO_4$, $HCO_3$, [($CF_3SO_2)_2N$], [$AsF_6$], alkylsulfonates, mono- or difluorinated alkyl sulfonates including perfluorinated alkylsulfonates, carboxylic acid anions, fluorinated carboxylic acid anions and metal halides.

Especially preferred are ionic liquids having the above formulae wherein A represents an anion selected from [PF6], [$BF_4$], [$OSO_2CF_3$], [$OSO_2(CF_2)_3CF_3$], [$OCO_2CF_3$], [$OCO_2$ ($CF_2)_3CF_3$], [$OCO_2CH_3$], nitrate, sulfate, hydrogen sulfate, hydrogen carbonate, acetate, trifluoroacetate, lactate, [($CF_3SO_2)_2N$], [B(alkyl)$_4$] wherein each alkyl can be the same or different and can be any straight chain or branched $C_1$ to $C_{10}$ alkyl (preferably $C_1$ to $C_6$ alkyl) group, [$SbF_6$]− and [$AsF_6$].

Even more preferred are ionic liquids of the above formulae wherein A represents an anion selected from [$PF_6$], [$BF_4$], [$OSO_2CF_3$], [$OSO_2(CF_2)_3CF_3$], [$OCO_2CF_3$], [$OCO_2(CF_2)_3CF_3$], [$OCO_2CH_3$], [($CF_3SO_2)_2N$], [B(alkyl)$_4$] wherein each alkyl can be the same or different and can be any straight chain or branched $C_1$ to $C_{10}$ alkyl (preferably $C_1$ to $C_6$ alkyl) group, [$SbF_6$]− and [$AsF_6$].

Other preferred ionic liquids include those wherein the anion is phosphate or an amide.

The anions [$PF_6$] (hexafluorophosphate), [$BF_4$] (tetrafluoroborate) and [($CF_3SO_2)_2N$] {bis[(trifluoromethyl)sulfonyl] amide or bistriflimide) are particularly preferred, especially for the imidazolium- and pyridinium-ation-based ionic liquids.

In a first embodiment, the present invention provides a process for the hydrogenation of a wide range of unsaturated aliphatic carbons, such as alkenes (including dienes, conjugated dienes, and trienes) and alkynes, which may contain a wide range of other functional groups. For example, using the present processes, it has been possible to achieve selective hydrogenation of the unsaturated carbon-carbon bond without significant reduction of e.g. carbonyl groups which may be present in the substrate. Thus, the use of ionic liquids in the present processes provides high, and at times very high, selectivities in such reactions.

A wide range of compounds containing at least one unsaturated carbon-carbon bond can be hydrogenated in accordance with the processes of the present invention. Suitable compounds that may be hydrogenated include compounds containing at least one C=C bond. The process of the present invention is also readily applicable to the hydrogenation of compounds containing multiple C=C bonds, e.g. one to four C=C bonds, preferably one to three C=C bonds The processes of the present invention can also be used to hydrogenate compounds containing at least one C≡C bond, as well as compounds containing multiple C≡C bonds (e.g. up to two C≡C bonds).

The processes of the present invention can be readily applied to hydrogenate substrates having a wide molecular weight range. For example, suitable substrates include compounds containing from 2 to 50 carbon atoms, preferably from 4 to 25 carbon atoms and more preferably from 6 to 20 carbon atoms.

The hydrogenation process of the first aspect of the present invention may be used to hydrogenate both compounds containing only C=C or C≡C functionalities, or compounds having a wide range of other functional groups in addition to the unsaturated carbon-carbon bond to be hydrogenated. In the latter case, it has been found that the present process can be highly chemoselective, i.e. it is possible to achieve selective hydrogenation of e.g. the C=C or C≡C bonds only, without hydrogenation of other functional groups.

For alkyne substrates, it is possible, by varying the catalyst and ionic liquid, to achieve partial hydrogenation, e.g. of the C≡C bond to form a C=C bond. Further, by varying the catalyst and reaction conditions, complete hydrogenation to the alkane may be achieved.

The hydrogenation process of the present invention may be applied to a wide range of compounds containing at least one unsaturated carbon-carbon bond, including alkenes, alkynes, esters, ethers, carboxylic acids, amines, amides, alcohols, fatty acids and esters thereof, steroids, prostaglandins, nitrites, aldehydes, ketones, isoprenoids, flavonoids, icosanoids, compounds containing a heterocyclic moiety wherein the heteroatom(s) can be nitrogen or oxygen, and compounds containing an aromatic moiety, such aryl-containing (e.g. phenyl-containing) compounds.

Preferred substrates include alkenes, alkynes, aldehydes, fatty acids and esters thereof, including those containing an α,β unsaturated carbonyl moiety.

Especially preferred carbonyl-containing compounds which are suitable substrates for the hydrogenation process of the present invention include those having the formula:

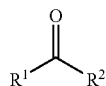

wherein:
$R^1$ is selected from hydrogen or $C_1$ to $C_{20}$ straight chain or branched alkyl or $C_3$ to $C_8$ cycloalkyl wherein said alkyl or cycloalkyl group may be substituted with 1-3 substituents independently selected from: $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, =O, $C_1$ to $C_6$ alkylamino, $C_1$ to $C_6$ dialkylamino, —CN, $COOR^3$, $CONR^3$ or $OR^3$ wherein $R^3$ is selected from H, $C_1$ to $C_{20}$ alkyl and $C_6$ to $C_{10}$ aryl; or $C_6$ to $C_{10}$ aryl wherein said aryl group may be substituted with 1-3 substituents independently selected from $C_1$ to $C_{10}$ alkyl, hydroxyl, F, $CF_3$, CN, $COOR^4$, $CONR^4$ or $OR^4$ wherein $R^4$ is selected from H, $C_1$ to $C_{20}$ alkyl; and $R^2$ represents $C_1$ to $C_{20}$ straight chain or branched alkenyl or $C_5$ to $C_8$ cycloalkenyl wherein said alkenyl or cycloalkenyl group may be substituted with 1-3 substituents independently selected from $C_1$ to $C_{20}$ alkyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, =O, $C_1$ to $C_6$ alkylamino, $C_1$ to $C_6$ dialkylamino, —CN, $COOR^3$, $CONR^3$ or $OR^3$ wherein $R^3$ is selected from H, $C_1$ to $C_{20}$ alkyl and $C_6$ to $C_{10}$ aryl; or $C_6$ to $C_{10}$ aryl wherein said aryl group may be substituted with 1-3 substituents independently selected from $C_1$ to $C_{10}$ alkyl, hydroxyl, F, $CF_3$, CN, $COOR^4$, $CONR^4$ or $OR^4$ wherein $R^4$ is selected from H and $C_1$ to $C_{20}$ alkyl.

Preferably, in the above compounds:
$R^1$ is selected from hydrogen; $C_1$ to $C_{20}$ straight chain or branched alkyl or $C_3$ to $C_8$ cycloalkyl wherein said alkyl or cycloalkyl group may be substituted with 1-3 substituents independently selected from: $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, =O or $OR^3$ wherein $R^3$ is selected from H, $C_1$ to $C_{20}$ alkyl and $C_6$ to $C_{10}$ aryl; or $C_6$ to $C_{10}$ aryl; and $R^2$ represents $C_1$ to $C_{20}$ straight chain or branched alkenyl or $C_5$ to $C_8$ cycloalkenyl wherein said alkenyl or cycloalkenyl group may be substituted with 1-3 substituents independently selected from $C_1$ to $C_{20}$ alkyl, $C_6$ to $C_{10}$ aryl, $C_8$-$C_{20}$ aralkyl, $C_8$-$C_{20}$ alkaryl, hydroxyl, F, $CF_3$, =O or $OR^3$ wherein $R^3$ is selected from H, $C_1$ to $C_{20}$ alkyl and $C_6$ to $C_{10}$ aryl; or $C_6$ to $C_{10}$ aryl.

Also preferred are compounds of the above formula wherein:
$R^1$ is selected from hydrogen; $C_1$ to $C_{10}$ straight chain or branched alkyl; and $R^2$ represents $C_1$ to $C_{20}$ straight chain or branched alkenyl or $C_5$ to $C_8$ cycloalkenyl wherein said alkenyl or cycloalkenyl group may be substituted with 1-3 substituents independently selected from $C_1$ to $C_{20}$ alkyl or $C_6$ to $C_{10}$ aryl.

Especially preferred are those compounds wherein:
$R^1$ is selected from hydrogen; $C_1$ to $C_{10}$ straight chain or branched alkyl; and $R^2$ represents $C_1$ to $C_{20}$ straight chain or branched alkenyl or $C_5$ to $C_8$ cycloalkenyl wherein said alkenyl or cycloalkenyl group may be substituted with $C_1$ to $C_{10}$ alkyl or phenyl.

The hydrogenation process of the present invention is particularly suitable for compounds as defined above wherein an α,β-unsaturated carbonyl moiety is present. In such compounds, it has been found that the carbon-carbon double bond can be hydrogenated selectively, i.e. the C=C bond can be hydrogenated in preference to the C=O bond.

Specific examples of suitable compounds include cinnamaldehyde, 2-octenal, citral, methylvinylketone, 3-cyclohexene-1-carboxaldehyde and benzylidine acetone.

Alkenes which may be hydrogenated using the present process include those having the formula:

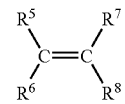

wherein:
$R^5$, $R^6$, $R^7$ and $R^8$ may be the same or different and each is independently selected from:
hydrogen;
$C_1$ to $C_{20}$ straight chain or branched alkyl or $C_3$ to $C_8$ cycloalkyl wherein said alkyl or cycloalkyl group may be substituted with 1-3 substituents independently selected from: $C_2$ to $C_{10}$ alkenyl, $C_5$ to $C_8$ cycloalkenyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, =O, $C_1$ to $C_6$ alkylamino, $C_1$ to $C_6$ dialkylamino, —CN, $COOR^3$, $CONR^3$ or $OR^3$ wherein $R^3$ is selected from H, $C_1$ to $C_{20}$ alkyl and $C_6$ to $C_{10}$ aryl;

$C_2$ to $C_{20}$ straight chain or branched alkenyl;
$C_5$ to $C_8$ cycloalkenyl; or
$C_6$ to $C_{10}$ aryl wherein said aryl group may be substituted with 1-3 substituents independently selected from $C_1$ to $C_{10}$ alkyl, hydroxyl, F, $CF_3$, CN, $COOR^4$, $CONR^4$ or $OR^4$ wherein $R^4$ is selected from H and $C_1$ to $C_{20}$ alkyl.

Preferably, $R^5$, $R^6$, $R^7$ and $R^8$ are the same or different and each is independently selected from:
hydrogen;
$C_1$ to $C_{20}$ straight chain or branched alkyl or $C_3$ to $C_8$ cycloalkyl wherein said alkyl or cycloalkyl group may be substituted with 1-3 substituents independently selected from: $C_2$ to $C_{10}$ alkenyl, $C_5$ to $C_8$ cycloalkenyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$ or $OR^3$ wherein $R^3$ is selected from H, $C_1$ to $C_{20}$ alkyl and $C_6$ to $C_{10}$ aryl; and $C_2$ to $C_{20}$ straight chain or branched alkenyl.

Also preferred are compounds wherein $R^5$, $R^6$, $R^7$ and $R^8$ are the same or different and each is independently selected from:
hydrogen;
$C_1$ to $C_{20}$ straight chain or branched alkyl or $C_3$ to $C_8$ cycloalkyl; and
$C_2$ to $C_{20}$ straight chain or branched alkenyl.

Especially preferred are compounds wherein $R^5$, $R^6$, $R^7$ and $R^8$ are the same or different and each is independently selected from hydrogen; $C_1$ to $C_{20}$ straight chain or branched alkyl; and $C_2$ to $C_{20}$ straight chain or branched alkenyl.

Particularly preferred are alkenes of the above formula wherein $R^5$ and $R^7$ each represents hydrogen.

Also preferred are alkenes of the above formula wherein $R^6$ and $R_8$ are each independently selected from $C_1$ to $C_{20}$ straight chain or branched alkyl, $C_3$ to $C_8$ cycloalkyl and $C_2$ to $C_{20}$ straight chain or branched alkenyl.

Preferred alkene substrates are those wherein $R^5$, $R^6$ and $R^7$ each represents hydrogen and $R^8$ is as defined in any preceding passage.

Thus, the hydrogenation process of the present invention may be applied to a wide range of alkenes including those having the formula

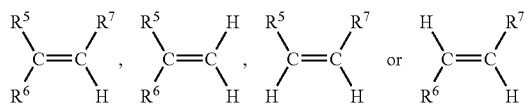

wherein $R^5$, $R^6$ and $R^7$ are as defined in any of the preceding passages.

Especially preferred alkene substrates include those as defined above wherein $R^5$, $R^6$, $R^7$ or $R^8$ represents a $C_2$ to $C_{20}$ straight chain or branched alkenyl.

The process of the present invention is also suitable for the hydrogenation of alkynes including those having the formula:

$$R^9C \equiv CR^{10}$$

wherein $R^9$ and $R^{10}$ are each independently selected from:
hydrogen;
$C_1$ to $C_{20}$ straight chain or branched alkyl or $C_3$ to $C_8$ cycloalkyl wherein said alkyl or cycloalkyl group may be substituted with 1-3 substituents independently selected from: $C_2$ to $C_{10}$ alkenyl, $C_5$ to $C_8$ cycloalkenyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, $=O$, $C_1$ to $C_6$ alkylamino, $C_1$ to $C_6$ dialkylamino, —CN, $COOR^3$, $CONR^3$ or $OR^3$ wherein $R^3$ is selected from H, $C_1$ to $C_{20}$ alkyl and $C_6$ to $C_{10}$ aryl; and
$C_6$ to $C_{10}$ aryl wherein said aryl group may be substituted with 1-3 substituents independently selected from $C_1$ to $C_{10}$ alkyl, hydroxyl, F, $CF_3$, CN, $COOR^4$, $CONR^4$ or $OR^4$ wherein $R^4$ is selected from H and $C_1$ to $C_{20}$ alkyl.

Particularly suitable alkyne substrates are those wherein $R^9$ and $R^{10}$ are each independently selected from:
hydrogen;
$C_1$ to $C_{20}$ straight chain or branched alkyl or $C_3$ to $C_8$ cycloalkyl wherein said alkyl or cycloalkyl group may be substituted with 1-3 substituents independently selected from: $C_6$ to $C_{10}$ aryl, $C_8$-$C_{20}$ aralkyl, $C_8$-$C_{20}$ alkaryl, $C_3$ to $C_8$ cycloalkyl, hydroxyl or $OR^3$ wherein $R^3$ is selected from H, $C_1$ to $C_{20}$ alkyl and $C_6$ to $C_{10}$ aryl; and
$C_6$ to $C_{10}$ aryl wherein said aryl group may be substituted with 1-3 substituents independently selected from $C_1$ to $C_{10}$ alkyl, hydroxyl, F or $OR^4$ wherein $R^4$ is selected from H and $C_1$ to $C_{20}$ alkyl.

Especially preferred are compounds wherein $R^9$ and $R^{10}$ are each independently selected from:
hydrogen;
$C_1$ to $C_{20}$ straight chain or branched alkyl or $C_3$ to $C_8$ cycloalkyl; and
$C_6$ to $C_{10}$ aryl wherein said aryl group may be substituted with 1-3 substituents independently selected from $C_1$ to $C_{10}$ alkyl, hydroxyl, F or $OR^4$ wherein $R^4$ is selected from H and $C_1$ to $C_{20}$ alkyl.

Also preferred are compounds wherein $R^9$ and $R^{10}$ are each independently selected from:
hydrogen;
$C_1$ to $C_{20}$ straight chain or branched alkyl or $C_3$ to $C_8$ cycloalkyl; and
$C_6$ to $C_{10}$ aryl wherein said aryl group may be substituted with 1-3 substituents independently selected from $C_1$ to $C_{10}$ alkyl, hydroxyl, or $OR^4$ wherein $R^4$ is selected from H and $C_1$ to $C_{10}$ alkyl.

Alkynes of the above formula wherein $R^9$ and $R^{10}$ are each selected from hydrogen, $C_1$ to $C_{10}$ alkyl which may be substituted by hydroxyl, or phenyl are particularly preferred.

Especially preferred alkynes of the above formula are those wherein at least one of $R^9$ or $R^{10}$ is hydrogen.

For the hydro-dehalogenation process of the present invention, the substrate may be any compound having at least one C—Cl, C—Br or C—I bond. Suitable substrates include those wherein the compound has the formula:

$$P—X$$

wherein:
P represents a group selected from:
$C_1$ to $C_{20}$ straight chain or branched alkyl or $C_3$ to $C_8$ cycloalkyl wherein said alkyl or cycloalkyl group may be substituted with 1-3 substituents independently selected from: $C_6$ to $C_{10}$ aryl, $C_8$-$C_{20}$ aralkyl, $C_8$-$C_{20}$alkaryl, $C_3$ to $C_8$ cycloalkyl, hydroxyl, F, $CF_3$, $=O$, $C_1$ to $C_6$ alkylamino, $C_1$ to Ce dialkylamino, —CN, $COOR^3$, $CONR^3$ or $OR^3$ wherein $R^3$ is selected from H, $C_1$ to $C_{20}$ alkyl and $C_6$ to $C_{10}$ aryl;
$C_6$ to $C_{10}$ aryl wherein said aryl group may be substituted with 1-3 substituents independently selected from $C_1$ to $C_{10}$ alkyl, hydroxyl, F, $CF_3$, CN, $COOR^4$, $CONR^4$ or $OR^4$ wherein $R^4$ is selected from H and $C_1$ to $C_{20}$ alkyl:
heteroaryl; or
heterocycloalkyl; and
X represents Cl, Br or I
Of these compounds, those wherein P represents:
$C_1$ to $C_{20}$ straight chain or branched alkyl or $C_3$ to $C_8$ cycloalkyl wherein said alkyl or cycloalkyl group may be substituted with 1-3 substituents independently selected from: $C_6$ to $C_{10}$ aryl, $C_8$-$C_{20}$ aralkyl, $C_8$-$C_{20}$ alkaryl, $C_3$ to $C_8$ cycloalkyl, hydroxyl;
$C_6$ to $C_{10}$ aryl wherein said aryl group may be substituted with 1-3 substituents independently selected from $C_1$ to $C_{10}$ alkyl, or hydroxyl;
heteroaryl; or
heterocycloalkyl are preferred.

Also preferred are those compounds wherein P represents:
$C_1$ to $C_{20}$ straight chain or branched alkyl or $C_3$ to $C_8$ cycloalkyl;

$C_6$ to $C_{10}$ aryl wherein said aryl group may be substituted with 1-3 substituents independently selected from $C_1$ to $C_{10}$ alkyl, or hydroxyl;

heteroaryl, wherein said heteroaryl group is a purine or pyrimidine; or heterocycloalkyl.

The hydro-dehalogenation process of the present invention is particularly suitable for compounds containing at least one C—Cl bond.

The present invention extends to any product obtainable by the processes herein described.

In the processes of the present invention, any suitable heterogeneous hydrogenation catalyst may be used. Particularly suitable are heterogeneous hydrogenation catalysts comprising nickel (e.g. Raney nickel), palladium, ruthenium, iridium, rhodium and platinum having an oxidation state of zero.

Especially preferred heterogeneous hydrogenation catalysts are those comprising palladium or platinum.

The heterogeneous hydrogenation catalysts are preferably in the form of a finely divided metal.

Typically, the catalyst is supported on an inert support, such as activated carbon, alumina, silica, silica-alumina, carbon black, graphite, titania, zirconia, calcium carbonate, and barium sulfate.

Preferred inert support materials are selected from activated carbon, carbon black, graphite, alumina or silica.

The hydrogenation catalysts for use in the present invention are heterogeneous, i.e. they do not dissolve in the ionic liquid, but instead remain as a suspension therein. However, the catalyst is preferably non-colloidal, i.e. the catalyst particle size, including support (if any) is greater than 20, preferably greater than 50, and preferably greater than 100 μm.

The processes of the present invention preferably employ as catalyst, a platinum or palladium group metal, particularly in supported form, e.g. on carbon, graphite or alumina.

The hydrogenating agent employed in the present process is typically molecular hydrogen or an organic or inorganic hydrogen transfer agent. Hydrogen transfer agents [see e.g. Johnstone et al., Chem. Rev. (1985), 85, 129 and. Brieger et al. Chem. Rev. (1974), 74, 567-580] are compounds which can release hydrogen and which are themselves oxidised. An example of such a hydrogen transfer agent is cyclohexene, which undergoes the following reaction in the presence of e.g. a palladium catalyst and an alkene substrate:

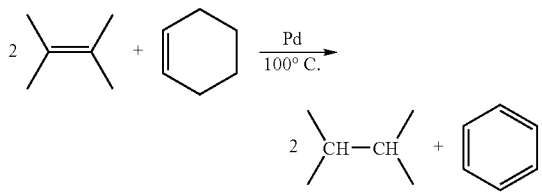

In such a process, the alkene is hydrogenated whilst the cyclohexene is oxidised to benzene.

Other suitable hydrogenating agents include molecular deuterium, HD, molecular tritium, HT, DT, or an organic or inorganic hydrogen, deuterium or tritium transfer agent.

Preferably, however, the hydrogenating agent is molecular hydrogen or an organic or inorganic hydrogen transfer agent. Molecular hydrogen is especially preferred as the hydrogenating agent.

The hydrogenation process of the present invention is preferably conducted at temperatures of from 15° C. to 200° C., preferably 15° C. to 140° C., and more preferably from 20° C. to 100° C. Good results are obtained at temperatures of 40° C. to 60° C.

Where a non-gaseous hydrogenating agent is employed, the reaction may be conducted at atmospheric pressure.

Where a gaseous hydrogenating agent such as molecular hydrogen is used, the reaction may be conducted at pressures of 101 kPa (i.e. atmospheric pressure) to 8 MPa. Typically, such reactions are conducted at pressures of from 150 kPa (preferably from 1 MPa) to 5 MPa and more preferably from 2.5 MPa to 4.5 MPa. Good results may be obtained using reaction pressures of 3 MPa to 4.2 MPa.

Hydrogenation reactions represent one of the largest uses of heterogeneous catalysts in the chemical industry. A range of reactions is possible from dehalogenation to simple reductions of alkene to selective reductions of α,β-unsaturated carbonyl containing molecules. Ionic liquids have not been used previously for any heterogeneously catalysed reactions and provide distinct advantages over many conventional organic and aqueous solvents where selectivity may be poor and/or there are problems with product separation and recycle of the catalyst/solvent system.

We believe we have found the first application of heterogeneous catalysts in ionic liquids for hydrogenation reactions. After the hydrogenation reaction, the hydrogenation catalysts remain suspended in the ionic liquid and are thus easily recyclable without the need to expose the catalyst to air or filter the catalyst from the reaction mixture. This increases the safety of hydrogenation processes especially where recycle of the catalyst is required. Ionic liquids also provide a medium where selectivity can be tuned for a given catalyst over conventional organic solvents.

Particular ionic liquids discussed herein include;
1-butyl-3-methylimidazolium hexafluorophosphate (bmimPF$_6$),
1-hexyl-3-methylimidazolium hexafluorophosphate (C$_6$mimPF$_6$),
1-octyl-3-methylimidazolium hexafluorophosphate (C$_8$mimPF$_6$),
1-decyl-3-methylimidazolium hexafluorophosphate (C$_{10}$mimPF$_6$),
1-dodecyl-3-methylimidazolium hexafluorophosphate (C$_{12}$mimPF$_6$),
1-ethyl-3-methylimidazolium bis((trifluoromethyl)sulphonyl)amide (emimNTf$_2$),
1-hexyl-3-methylimidazolium bis((trifluoromethyl)sulphonyl)amide (C$_6$ mimNTf$_2$),
1-hexylpyridinium tetrafluoroborate (C$_6$py BF$_4$),
1-octylpyridinium tetrafluoroborate (C$_8$py BF$_4$),
1-butyl-3-methylimidazolium tetrafluoroborate (bmimBF$_4$).

Unless indicated otherwise, the terms used herein have the meanings as indicated below:

"Alkyl" (including alkyl portions of alkyoxy, alkaryl, aralkyl, alkylamino, dialkylamino) represents straight and branched carbon chains containing from 1 to 40 carbon atoms, preferably 1 to 40 carbon atoms, and more preferably 4 to 12 carbon atoms.

"Cycloalkyl" represents saturated carbocyclic rings branched or unbranched containing from 3 to 20 carbon atoms, preferably 3 to 8 carbon atoms. Such cycloalkyl groups include cyclopentyl and cyclohexyl.

"Heterocycloalkyl" represents a saturated, branched or unbranched carbocyclic ring containing from 3 to 12 carbon atoms, preferably from 4 to 6 carbon atoms, wherein the carbocyclic ring is interrupted by 1 to 3 heteroatom moieties selected from —O—, or —N(C$_1$ to C$_6$ alkyl), or NH. Such heterocycloalkyl groups include 2- or 3-tetrahydrofuranyl, 2-, 3- or 4-piperidinyl, 2-, 3- or 4-piperizinyl, morpholinyl, 2- or 3-pyrrolidinyl and 2- or 4-dioxanyl.

"Alkenyl" represents straight and branched carbon chains having at least one carbon to carbon double bond and containing from 2 to 40 carbon atoms, preferably 2 to 20 carbon atoms and more preferably from 2 to 12 carbon atoms. Thus, the term "alkenyl" as used herein includes dienes (including conjugated dienes) trienes and tetraenes.

"Cycloalkenyl" represents saturated carbocyclic rings branched or unbranched containing from 3 to 20 carbon atoms, preferably 3 to 8 carbon atoms, wherein the ring contains at least one C═C bond. Cyclohexenyl and cyclopentenyl are particularly preferred cycloalkenyl groups.

"Alkynyl" represents straight and branched carbon chains having at least one carbon to carbon triple bond and containing from 2 to 20 carbon atoms, preferably 2 to 20 carbon atoms and more preferably from 2 to 12 carbon atoms.

"Aryl" including aryl moieties in e.g. aralkyl represents a carbocyclic group containing from 6 to 15 carbon atoms (preferably from 6 to 10 carbon atoms) and having at least one aromatic ring, with all available substitutable carbon atoms of the carbocyclic group being intended as possible points of attachment. Preferred aryl groups include phenyl and naphthyl. Unless otherwise indicated, the term "aryl" includes such carbocyclic groups being optionally substituted with, 1 to 3 of the following substituents: $C_1$ to $C_6$ alkyl, OH, O($C_1$ to $C_6$ alkyl), phenoxy, $CF_3$, ($C_1$ to $C_6$ alkyl)amino, di($C_1$ to $C_6$ alkyl)amino, —COO($C_1$ to $C_6$ alkyl) or $NO_2$.

"Heteroaryl" represents cyclic groups having at least one heteroatom selected from —O— or —N—, said heteroatom interrupting a carbocyclic ring structure and having a sufficient number of delocalised pi electrons to provide aromatic character, with the aromatic heterocyclic groups preferably containing from 2 to 14 carbon atoms. Suitable heteroaryl groups include pyridine, indole, imidazole, pyridazine, pyrazine, oxazole, triazole, pyrazole, and purines and pyrimidines.

The present invention will be discussed in more detail by way of the following examples and figures:

FIG. 1a: Variation in product distribution with time following cinnamaldehyde 1 reduction over 5 wt % Pt/graphite catalyst in $bmimPF_6$.

Figure 1B:
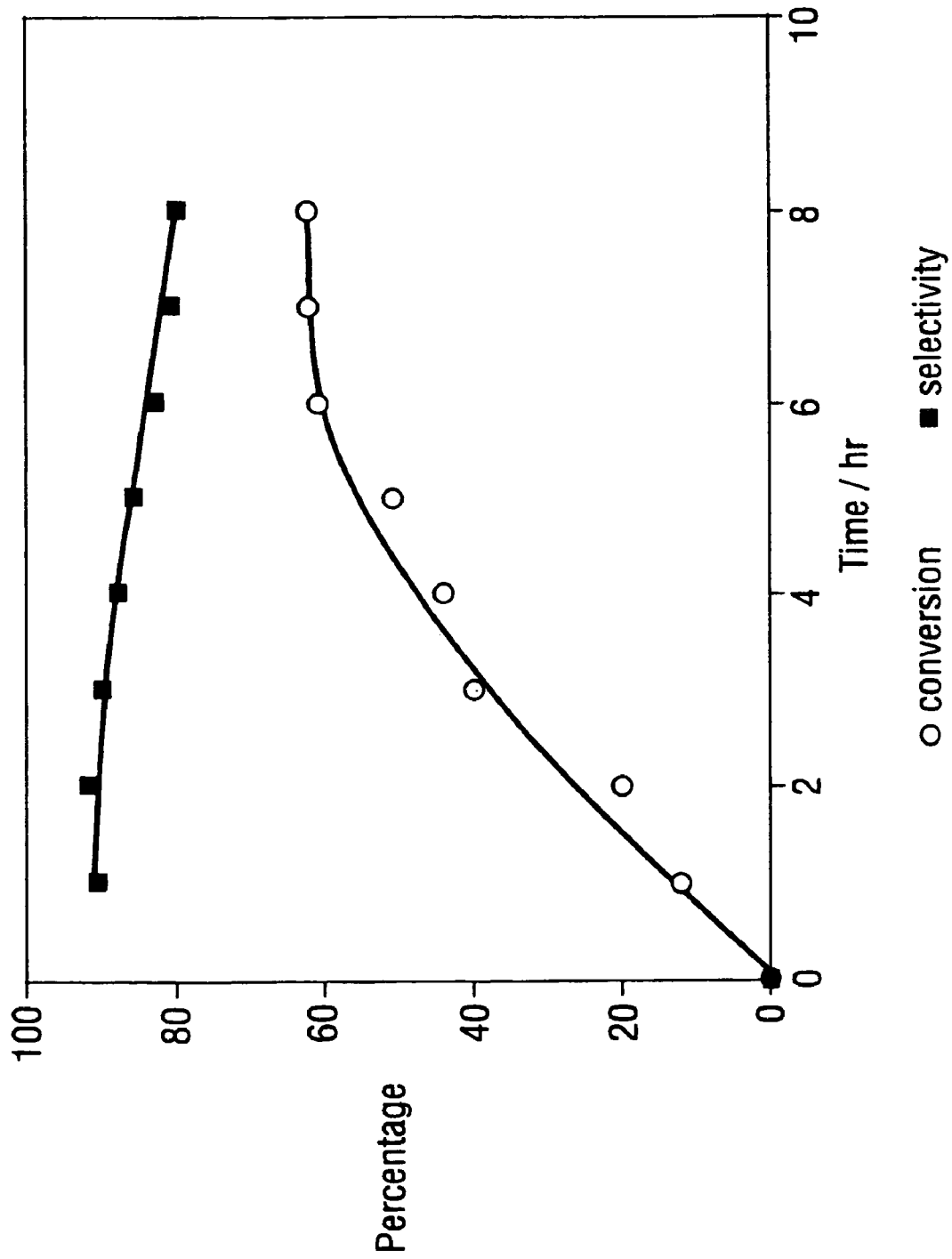

FIG. 1b: Variation in conversion and selectivity towards 2 with time following cinnamaldehyde reduction over 5 wt % Pt/graphite catalyst in $bmimPF_6$.

Figure 2A:
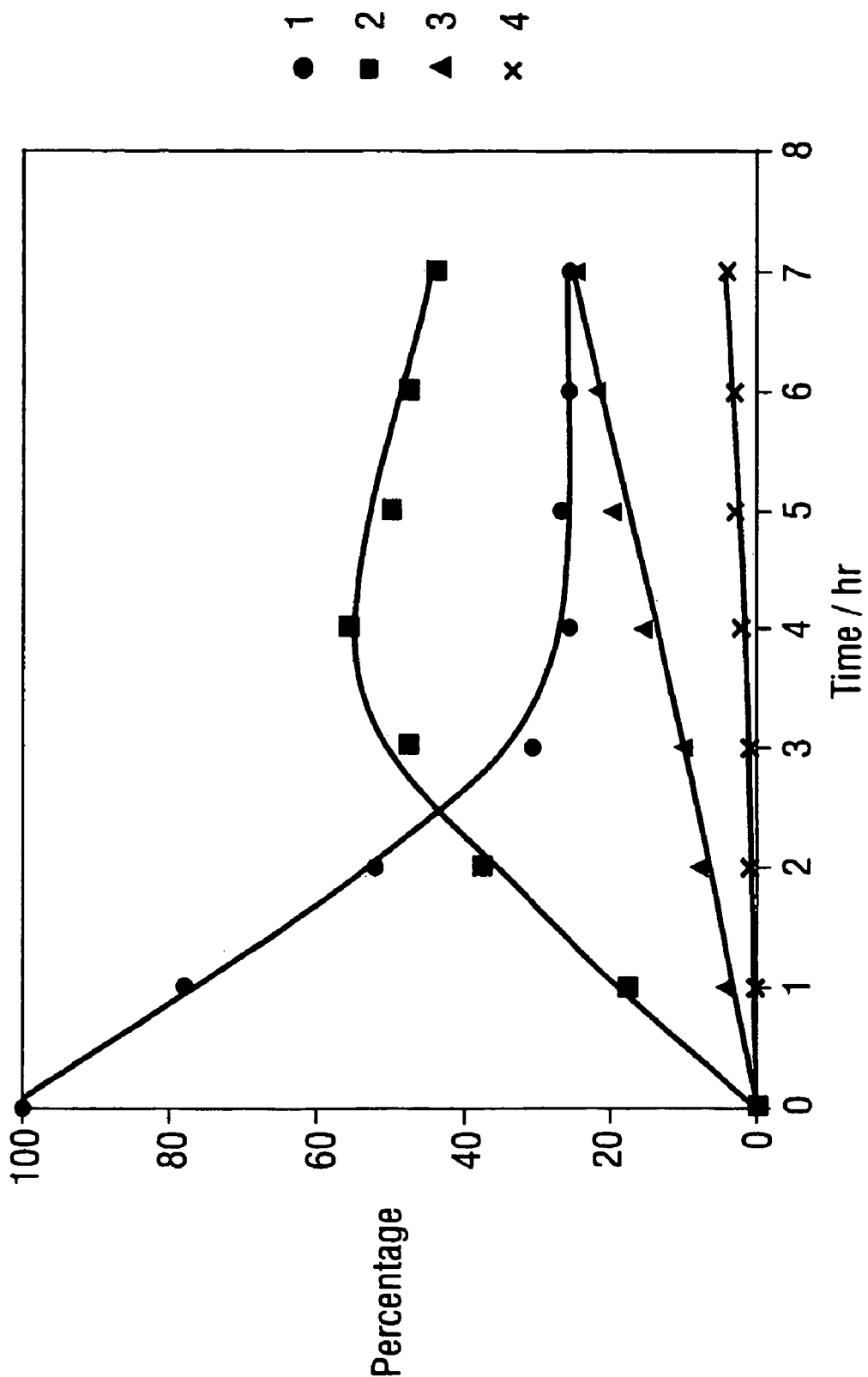

FIG. 2a: Variation in product distribution with time following cinnamaldehyde 1 reduction over 5 wt % $Pt/Al_2O_3$ catalyst in bmimPFe.

Figure 2B:
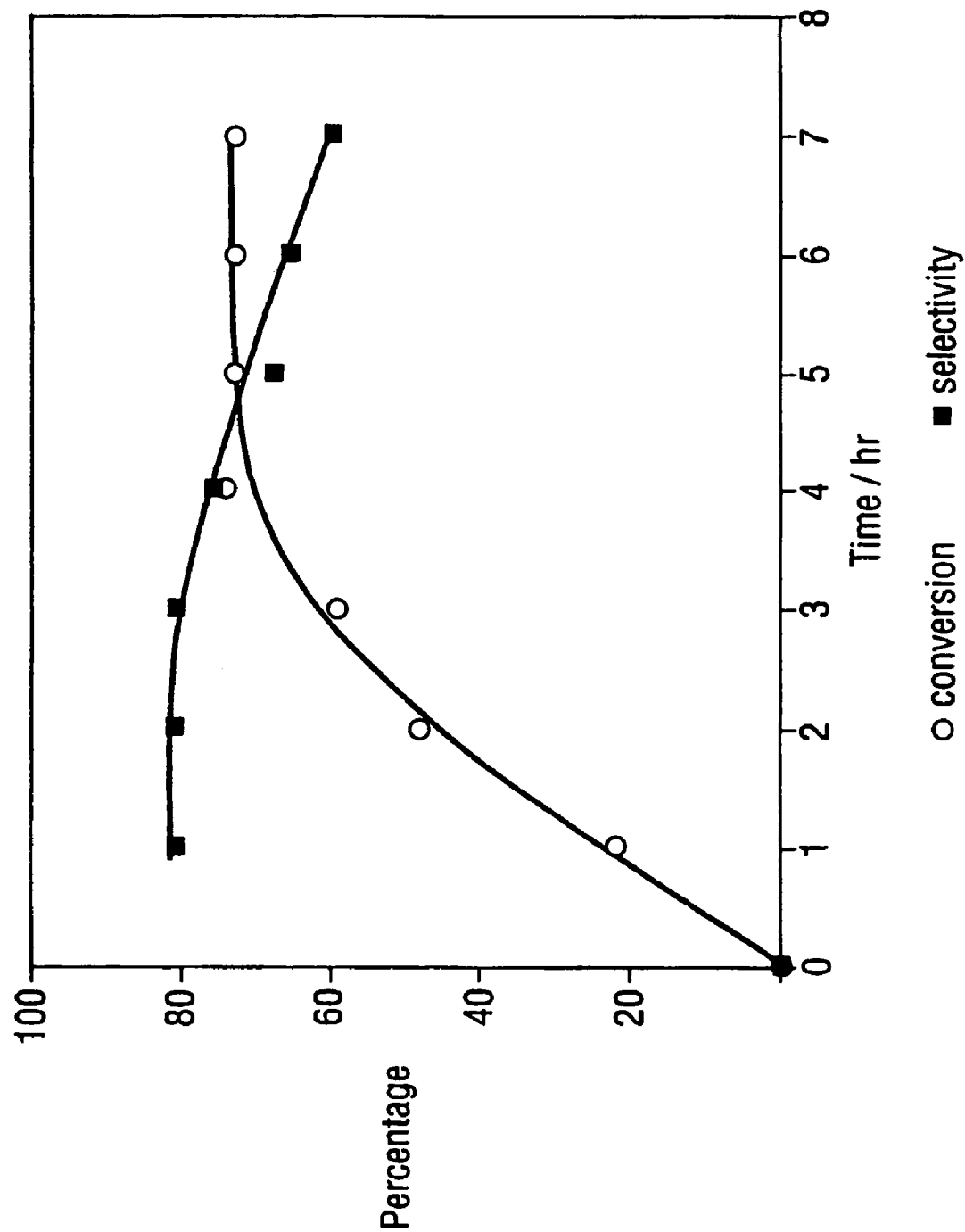

FIG. 2b: Variation in conversion and selectivity towards 2 with time following cinnamaldehyde reduction over 5 wt % $Pt/Al_2O_3$ catalyst in $bmimPF_6$.

Figure 3A:
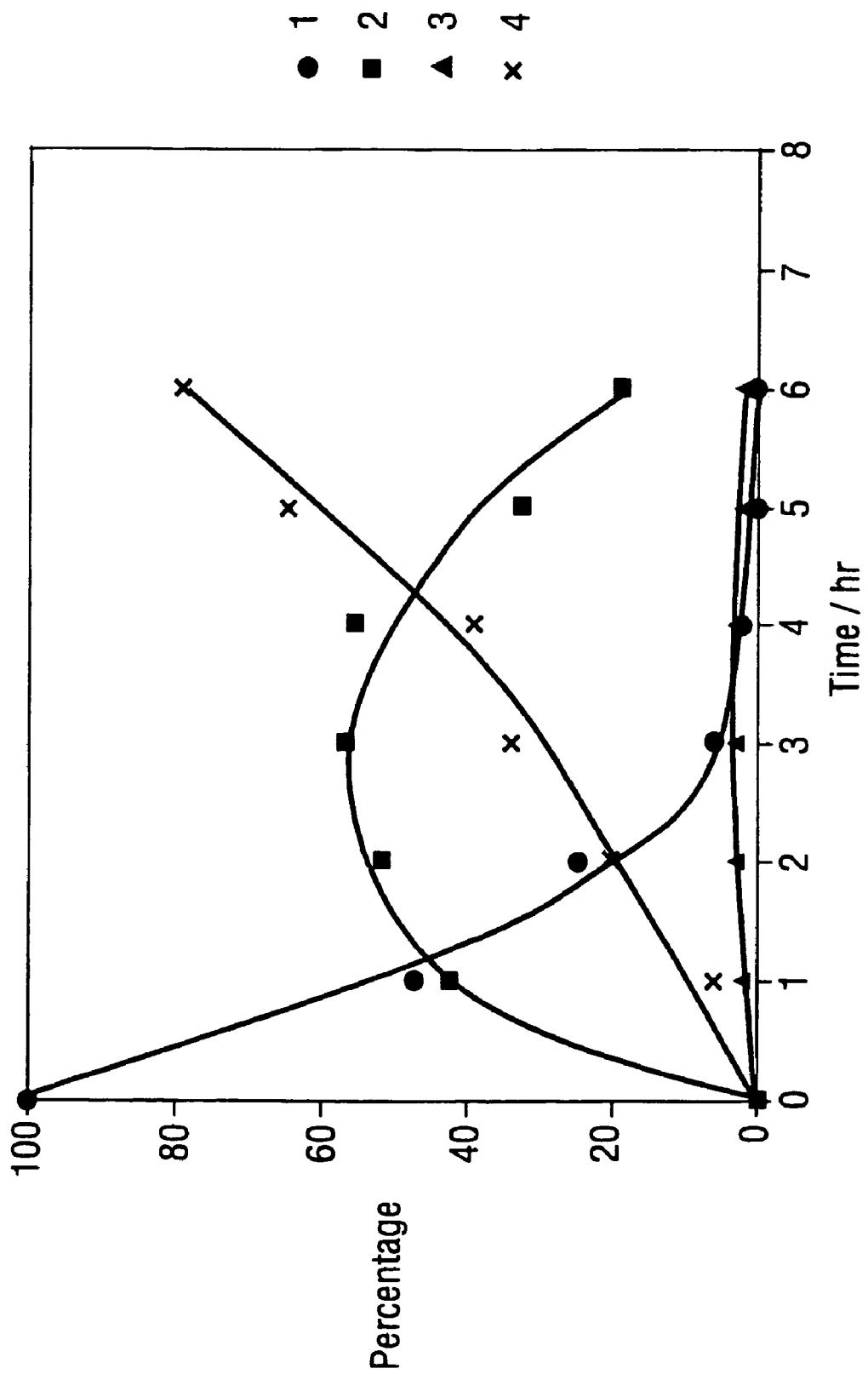

FIG. 3a: Variation in product distribution with time following cinnamaldehyde 1 reduction over 5 wt % Pt/graphite catalyst in propan-2-ol.

FIG. 3b: Variation in conversion and selectivity towards 2 with time following cinnamaldehyde reduction over 5 wt % Pt/graphite catalyst in propan-2-ol.

Figure 4:
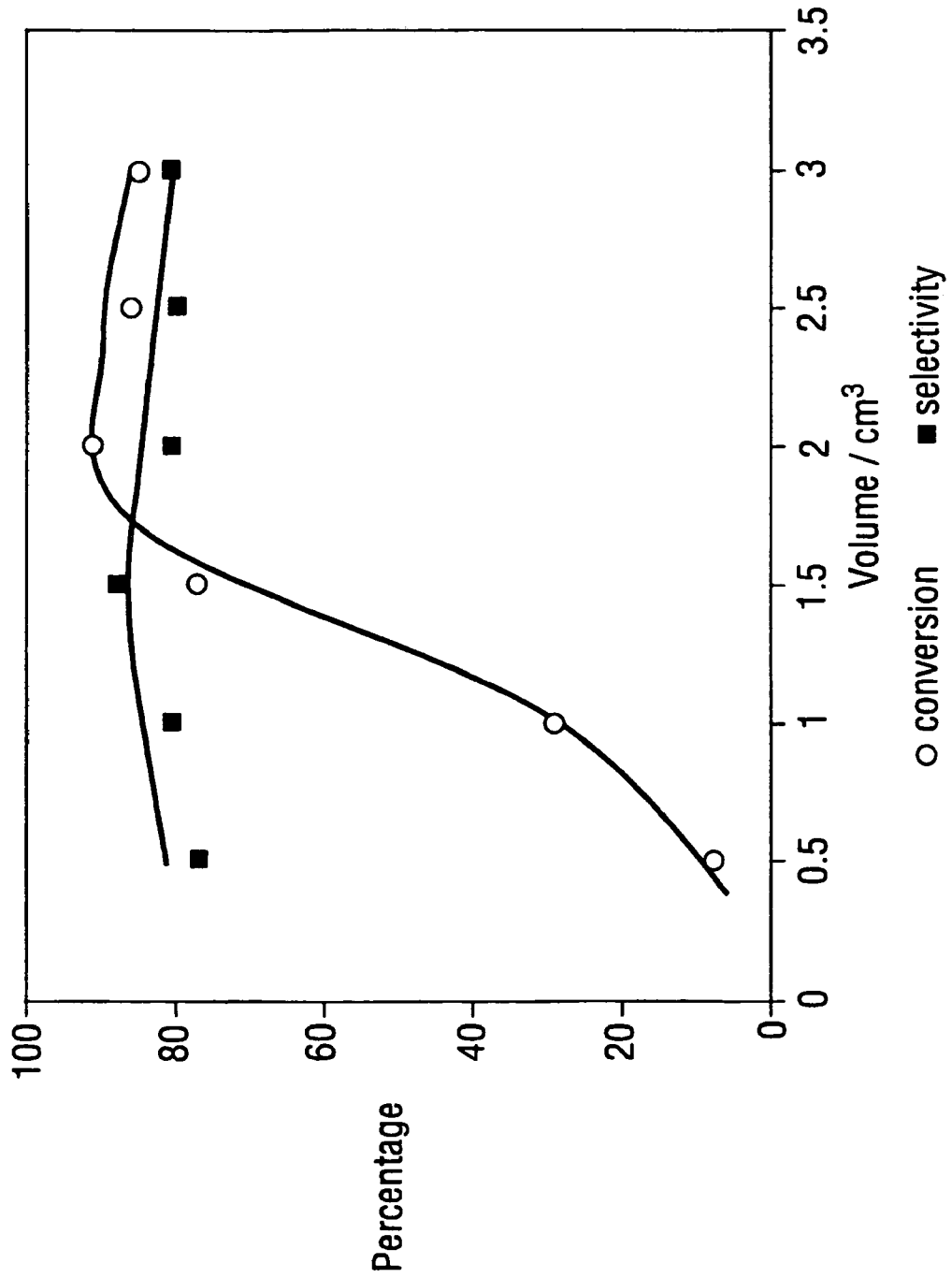

FIG. 4: Variation in conversion and selectivity towards 2 with ionic liquid volume following cinnamaldehyde reduction over 5 wt % Pt/graphite catalyst in $emimNTf_2$.

Figure 5:
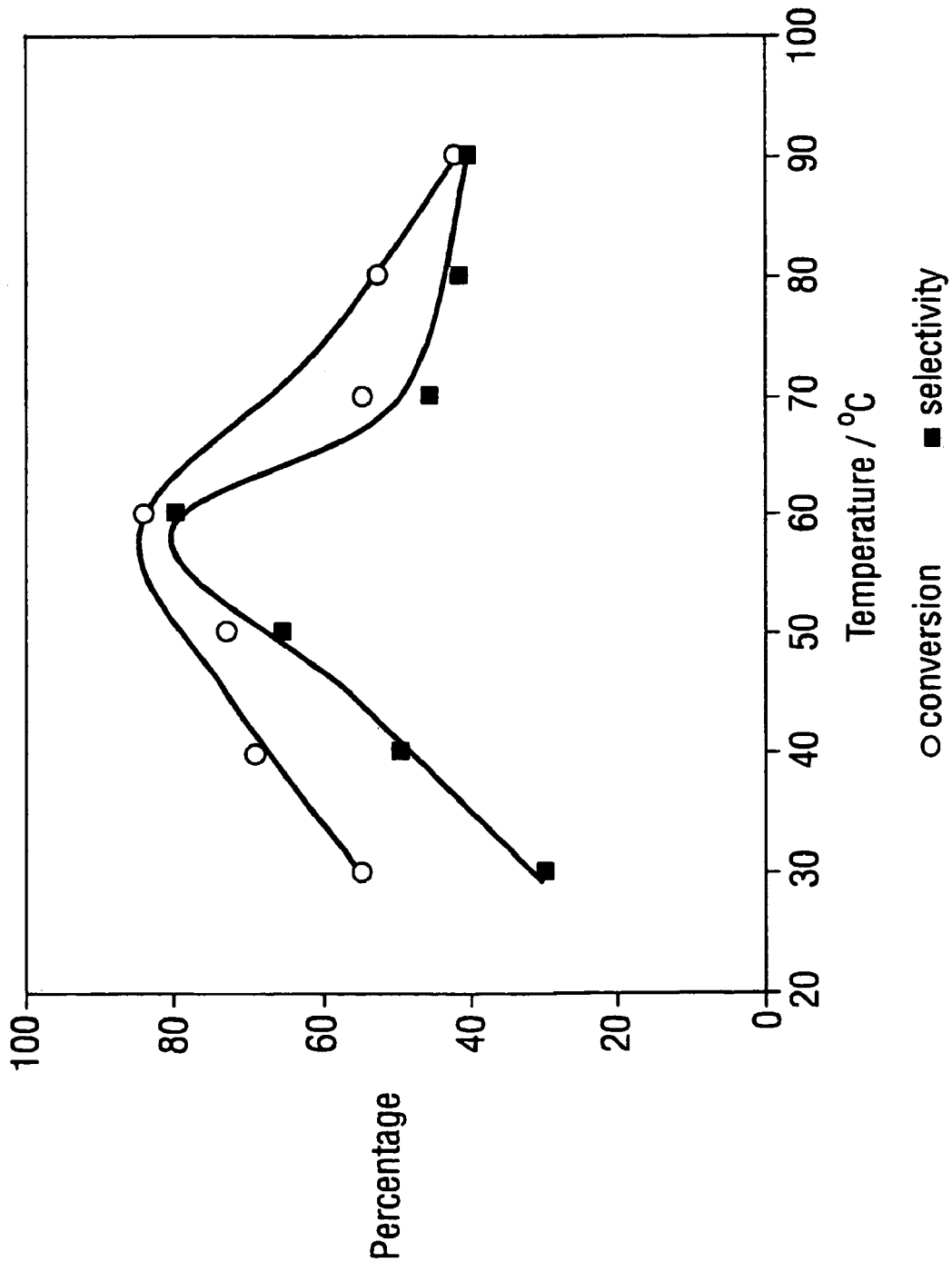

FIG. 5: Variation in conversion and selectivity towards 2 with temperature following cinnamaldehyde reduction over 5 wt % Pt/graphite catalyst in $emimNTf_2$.

Figure 6:
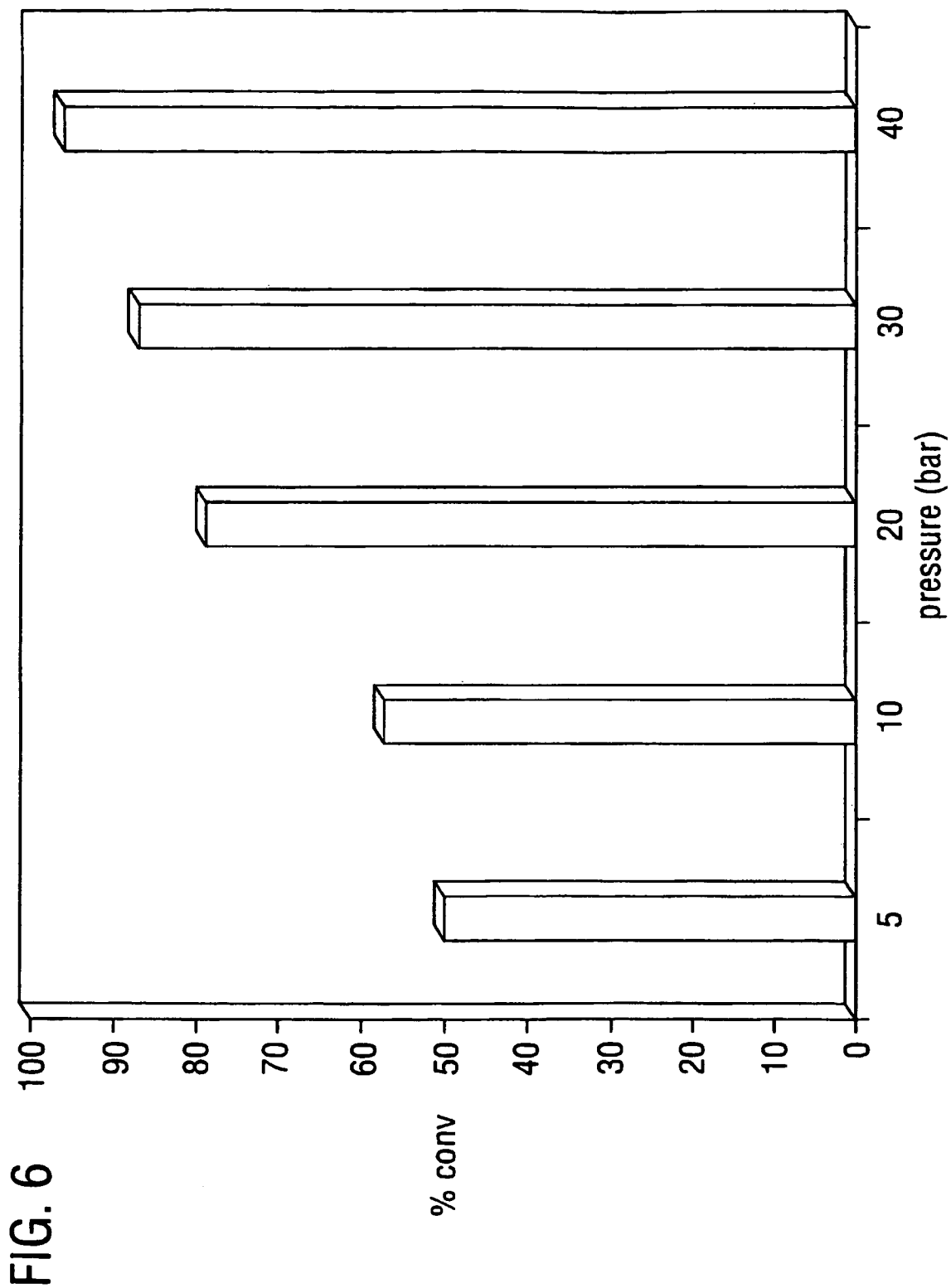

FIG. 6: Variation in conversion of 1 to 3 with pressure following cinnamaldehyde reduction over 10 wt % Pd/C catalyst in $bmimBF_4$.

Figure 7:
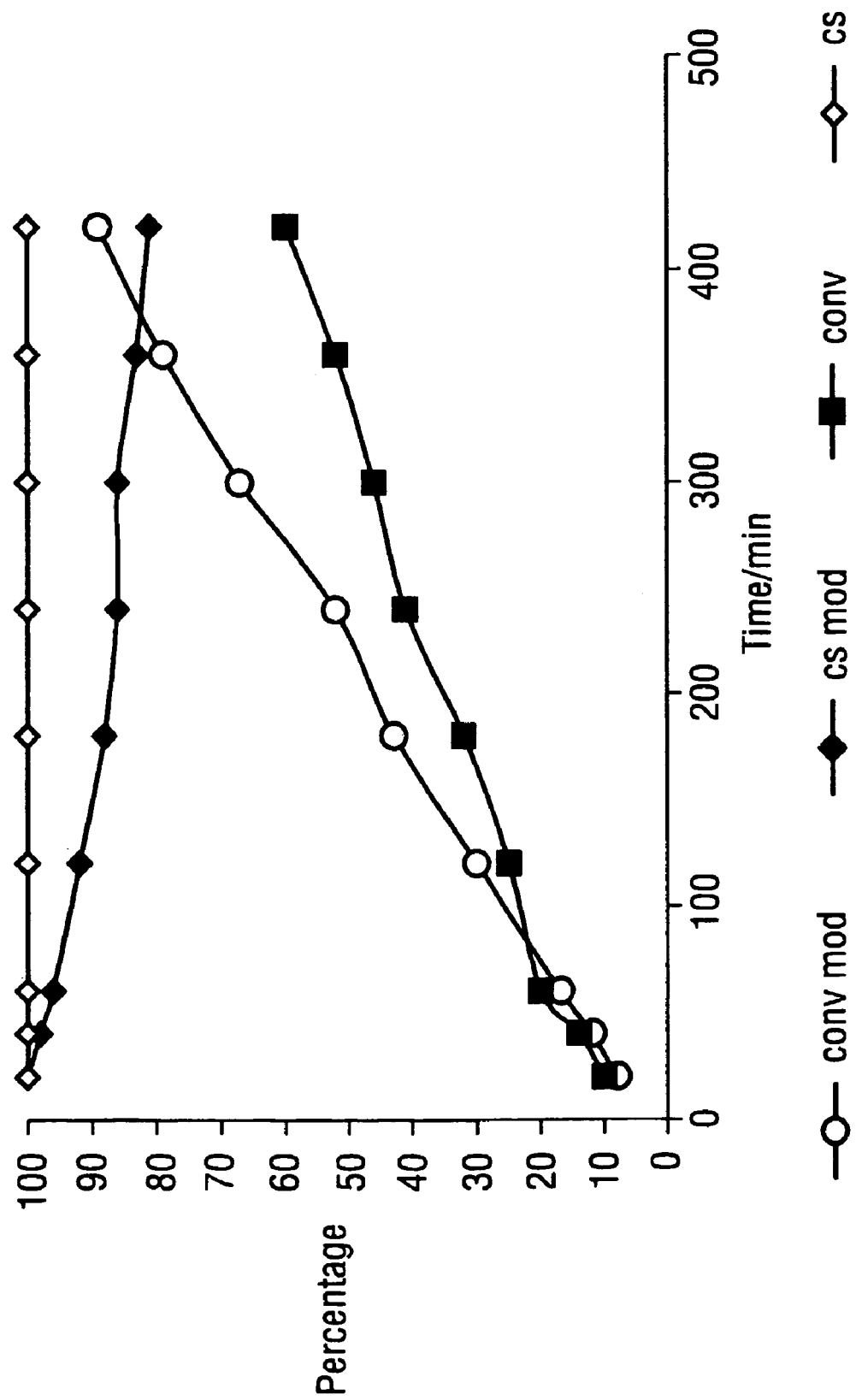

FIG. 7: Kinetic study for the conversion (conv) and chemoselectivity (cs) in the hydrogenation of citral to citronellal in 10 wt % Pd/C and 10 wt % Pd/C modified catalysts in $bmimBF_4$ FIG. 8: Variation in conversion of 1-nonyne and selectivity towards 1-nonene with time following 1-nonyne reduction over 10 wt % Pd/C catalyst in $C_6PyBF_4$ at 30° C. and $3\times10^5$ Pa.

Figure 9A:
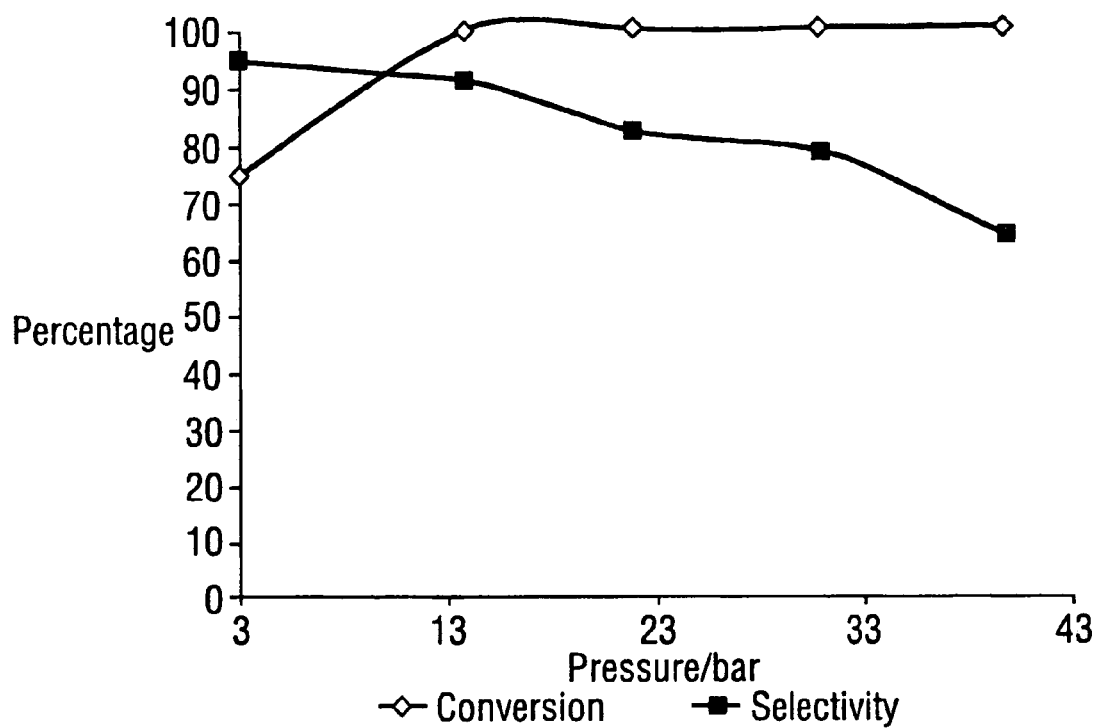

FIG. 9a: Variation in conversion and selectivity towards styrene with pressure following phenyl acetylene reduction over 5 wt % $Pd/CaCO3$ at 30° C. after 4 hr.

Figure 9B:
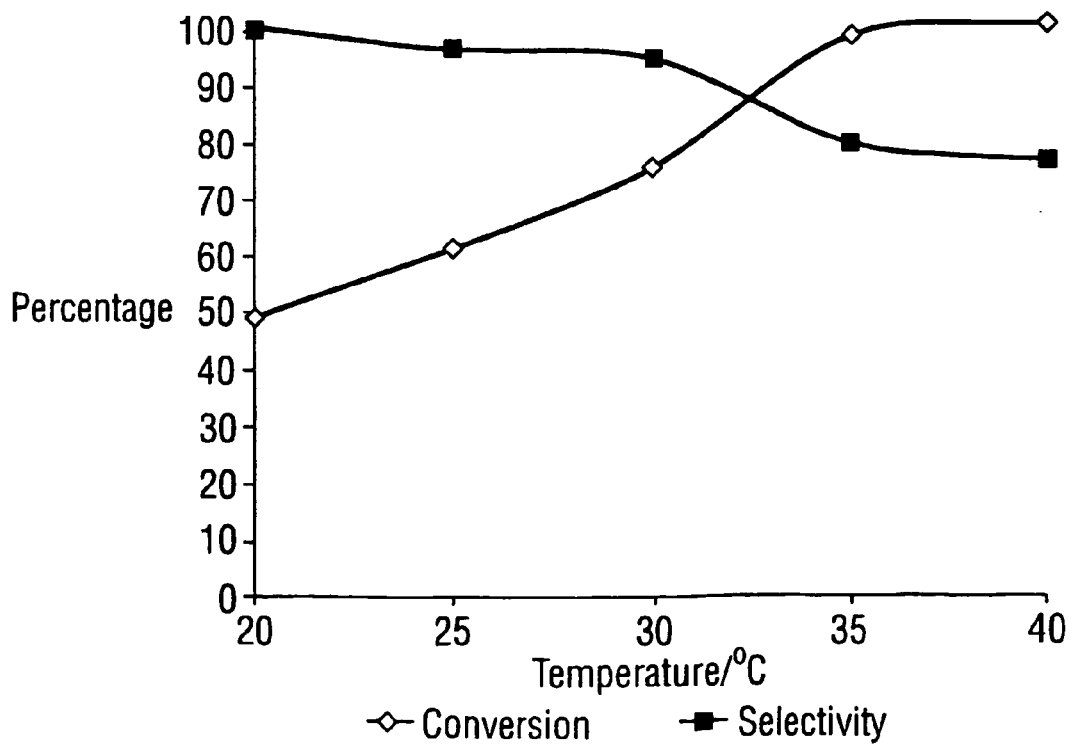

FIG. 9b: Variation in conversion and selectivity towards styrene with temperature following phenyl acetylene reduction over 5 wt % $Pd/CaCO_3$ at $3\times10^5$ Pa for 4 hr.

Figure 9C:
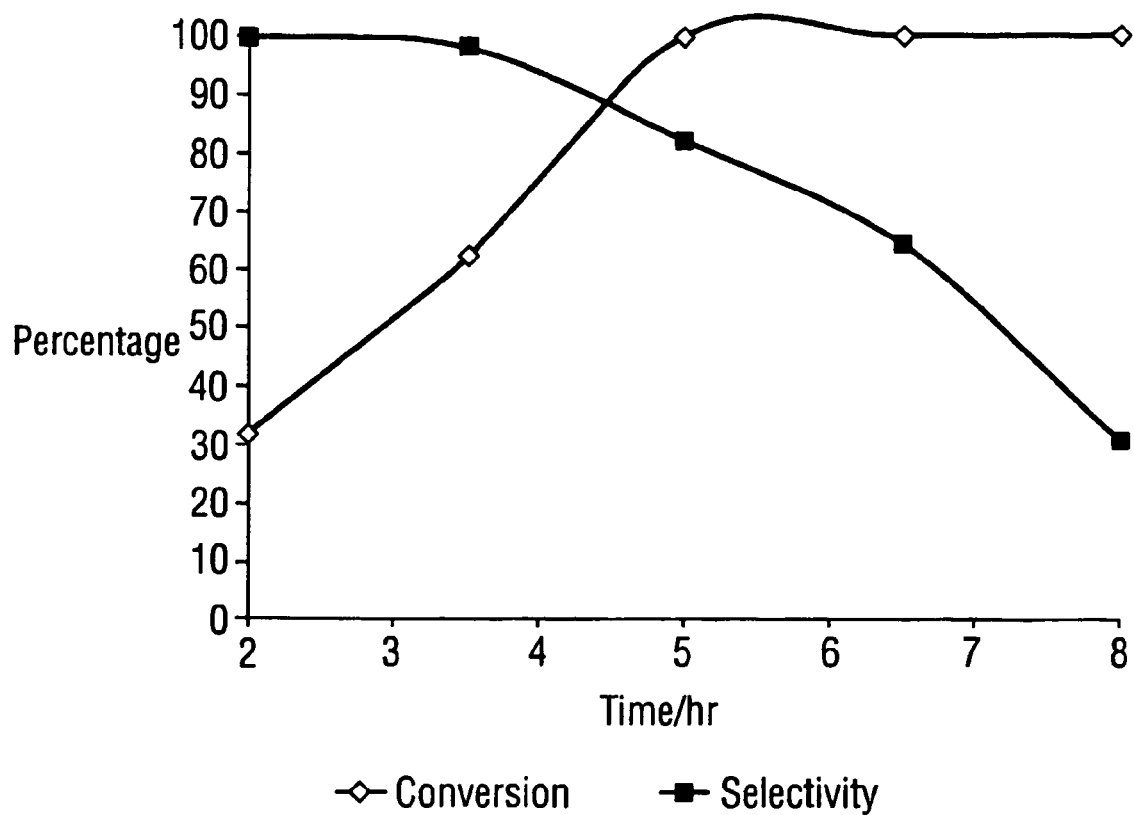

FIG. 9c: Variation in conversion and selectivity towards styrene with time following phenyl acetylene reduction over $Pd/CaCO_3$ at $3\times10^5$ Pa & 30° C.

EXAMPLES

In the examples hereinafter, all reactions were carried out in a Baskerville mini autoclave. For all results, the selectivity is defined as follows:

$$\% \text{ selectivity } n = \frac{\% n}{\text{Sum of the \% products formed}} \times 100$$

where % n is the percentage yield of n.

The ionic liquids for use in the present invention including those employed in the following examples can be made by process such as those disclosed in WO 01/40146.

Example 1

1.0 Hydrogenation of Cinnamaldehyde Using Platinum Based Catalysts

Cinnamaldehyde, 1, can undergo reduction using hydrogen gas over a heterogeneous catalyst to produce three products, cinnamylalcohol, 2, hydrocinnamaldehyde, 3, and 3-phenylpropanol, 4. The reactions may proceed in two different pathways 1 to 2 to 4 or 1 to 3 to 4 as shown below. This reaction has been studied extensively by many workers with an aim to control the selectivity and promote the formation of cinnamylalcohol and hydrocinnamaldehyde without further reduction to 3-phenylpropanol. These investigations have concentrated on the effect of promoters on the catalyst such as doping with tin or using zeolite based catalysts. The aim of this study was to develop ionic liquids for heterogeneously catalysed reactions and specifically in this case to investigate whether the solvent could act as a promoter without the need to use expensive catalysts.

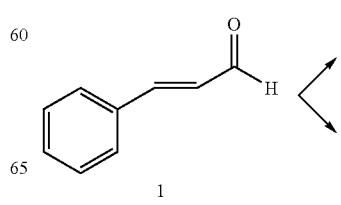

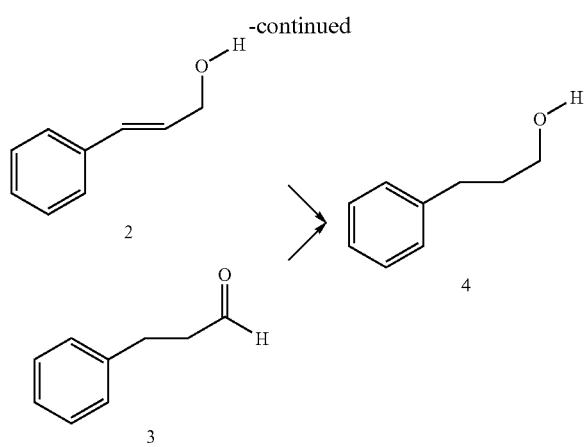

Each system was compared with propan-2-ol as a benchmark solvent. In the best cases, recycle of the catalyst was attempted. This research shows the potential of ionic liquids to promote selectivity in heterogeneously catalysed reactions with the ability to recycle the catalyst without the need to reactivate it. Some mechanistic details have also been studied and show that isomerisation between 2 and 3 dominates the overall selectivity of the reduction rather than secondary reduction processes.

Unless otherwise stated the reactions were performed under a hydrogen pressure of 4 MPa and a temperature of 60° C. The platinum catalysts were pre-reduced in flowing hydrogen at 350° C. for 1 h. Ionic liquid (2 ml), 17.5 mg (5 wt % Pt catalyst), and cinnamaldehyde 0.5 ml (substrate/metal~800/1) were introduced to the autoclave and purged three times with argon. Hydrogen at 4 MPa was introduced and the autoclave heated to the required temperature. The reaction is left to stir for 6 h, upon which the reaction is cooled and the pressure released.

The reaction products were extracted using diethyl ether (2×10 ml), which removes all the organic products whilst maintaining the catalyst in the ionic liquid. Product selectivities and conversions were determined using GC-FID.

Table 1 summarises the results of an initial screening for the hydrogenation of cinnamaldehyde using 5% Pt/graphite in a range of ionic liquids.

TABLE 1

Cinnamaldehyde hydrogenation[a] variation with ionic liquid type using 5% Pt/graphite catalyst.

| Solvent | % Conversion | % Selectivity 2 |
|---|---|---|
| emimNTf$_2$ | 85 | 81 |
| C$_6$mimNTf$_2$ | 72 | 83 |
| C$_6$mimPF$_6$ | 50 | 46 |
| bmimBF$_4$ | 7 | 76 |
| bmimPF$_6$[a] | 47 | 83 |
| bmimPF$_6$[b] | 49 | 81 |
| bmimPF$_6$[c] | 60 | 81 |
| propan-2-ol[d] | 89 | 53 |

[a]reactions carried out at 6 hours at 60° C. and 4 MPa H$_2$;
[b]ionic liquid recycled;
[c]nitric acid added.
[d]3 hours reaction (at 6 hours the selectivity = 18%)

These results suggest that the hydrogenation of cinnamaldehyde is inhibited in [BF$_4$]$^-$ ionic liquids and that [NTf$_2$]$^-$ based systems are more active than those containing [PF$_6$]$^-$. Although the conversions for the ionic liquid systems were lower in comparison with propan-2-ol, higher selectivity was maintained at high conversion. It should be noted that in all the ionic liquid reactions, the yield of 4 was negligible whereas in the propan-2-ol reactions this formed the majority of product at 100% conversion. Other anions tested included nitrate, sulfate, hydrogensulphate, hydrogencarbonate, acetate, trifluoroacetate and (S)-lactate; these resulted in little or no conversion. Replacing Pt/graphite with Pt/alumina resulted in lower selectivities and conversions in general.

The addition of trace amounts of nitric acid increased the yield from 47 to 60% without any significant effect on selectivity. It is not clear as yet whether the acid changes the nature of the catalyst surface or influences the redox chemistry of the reaction. The addition of acid is detrimental to the workup, however, since it increases the ionic liquid solubility in common organic solvents, which results in leaching of both the catalyst and the ionic liquid into the organic phase during extraction.

A number of reductions were also carried out in pyridinium and ammonium ionic liquids with little success. Pyridinium and ammonium BF$_4$ and bistriflimides liquids showed no reaction as was the case for pyrollidinium and piperidinium bistriflimides. It is also worth noting that all of the 'solid' solvents employed (for example pyridinium PF6 systems) gave no reaction despite melting below the reaction temperature of 60° C.

From the initial screening, imidazolium ionic liquids achieve the highest yields and selectivity with the trend [NTf$_2$]$^-$>[PF$_6$]$^-$>[BF$_4$]$^-$. The best system, emimNTf$_2$, is hydrophobic enabling chloride removal efficient simply by washing with water. It has very low viscosity, which makes it easy to handle and allow for catalyst dispersion.

1.1 Kinetic Study on the Hydrogenation of Cinnamaldehyde

Two kinetic studies were carried out to compare the effect of catalyst support. FIGS. 1a, 1b, 2a and 2b show the hydrogenation of cinnamaldehyde using Pt/graphite or Pt/alumina in bmimPF$_6$. In both cases, the reaction stops after 5-7 hrs with the conversion rate slowing significantly after 3-5 hrs. Initially the selectivity is high towards cinnamylalcohol 2 however, with increasing reaction time some hydrocinnamaldehyde 3 and 3-phenylpropanol 4 forms. We believe that the formation of 3 occurs because of isomerisation between 2 and 3 catalysed by the supported catalyst in the ionic liquid. This is more pronounced in the case of Pt/Al$_2$O$_3$ catalysts where a maximum in the selectivity is clearly observed. In both reactions only trace (<2%) of the totally saturated product, 4, is formed. Separate experiments studying the isomerisation of cinnamylalcohol in the presence of Pt catalysts in a range of ionic liquids under an inert atmosphere at 60° C. gave up to 60% isomerisation to hydrocinnamaldehyde after 4 hrs. (Note the blank reactions and those performed in propan-2-ol gave negligible conversion). In agreement with the hydrogenation experiments Pt/alumina is more effective than Pt/graphite for the isomerisation.

These kinetic runs may be compared with a similar study using Pt/graphite in propan-2-ol performed at 60° C., shown in FIGS. 3a and 3b. More conversion is found in propan-2-ol, however, the selectivity towards 2 is poor above 75% conversion. At lower temperatures the selectivity and conversion are both poor.

Catalyst deactivation is likely to be the cause of the conversion being limited. To assess whether the substrate or ionic liquid was causing the deactivation, a blank experiment in which the hydrogenation was carried out under normal experimental conditions for 6 hrs without any substrate, cooled, the substrate was added and the reaction performed once more. Under these conditions, no reaction was observed indicating that the ionic liquid, and not the substrate/products, was responsible for the catalyst poisoning.

Poisoning by the ionic liquid could be the result of a number of variables, for example pore blocking, the blocking sites by strongly adsorbed species or halide contamination from the ionic liquid manufacture. Experiments were performed in the presence of trace halide from HCl and NaCl to assess the contribution of halide deactivation. No conversion was observed in these reactions showing that firstly the ionic liquids are used were virtually halide free and secondly, absence of halide impurities is important if these reactions are to proceed. The major consequence of this is that unless electrolysis is performed prior to use, these reactions are limited to hydrophobic ionic liquids, which may be washed with water to remove trace chloride.

Deactivation via strongly adsorbed species was investigated by varying the ionic liquid to catalyst/substrate ratio. The results of this study are shown in FIG. 4.

Varying the volume of ionic liquid used resulted in little variation in selectivity; however, the conversion was found to vary strongly. Significantly, a maximum in conversion is observed. This occurs at smaller ionic liquid volumes than had been used previously.

1.2 Recycle

The initial screening results (Table 1) showed that although it was possible to recycle the ionic liquid, however, in general recycle of the ionic liquid/platinum catalyst resulted in little reaction. Using the optimum conditions found from FIG. 4, recycle of the catalyst and ionic liquid was possible. The ionic liquid was simply extracted without removing the catalyst resulting in 99% of the starting material and products being removed, and fresh cinnamaldehyde added. Using this system, 42% conversion and 80% selectivity was achieved after 6 hours compared with 85% conversion and 81% selectivity for the fresh catalyst system. It should be noted that, extraction results in little transfer of catalyst to the extracting phase and on recycle the catalyst was not pre-activated in hydrogen. As described in the experimental, the normal procedure for the reaction with platinum catalysts is to activate the catalyst in flowing hydrogen at temperature prior to reaction. Without this procedure little reaction occurs and the fact that recycle is possible without further activation shows a significant benefit of using ionic liquids as solvents over conventional organic solvent Osystems.

1.3 Temperature Study on the Effect of Conversion/Selectivity

Optimisation with respect to temperature was also performed and the results are shown in FIG. 5.

Selectivity and conversion map each other with a maximum in both at 60° C. The selectivity maximum presumably indicates a balance between adsorption and isomerisation. At low temperatures, desorption is low and hence secondary reactions occur whereas at higher temperature isomerisation from 2 to 3 is favoured. Two competing effects may also cause the maximum in conversion, reaction rate and hydrogen solubility. The former rises with temperature whereas the latter drops. Above 90° C. significant polymerisation occurred.

1.4 Hydrogenation of Cinnamaldehyde in $C_n$-Methylimidazolium Ionic Liquids

A study into the effect of increasing alkyl chain length ($C_4$-$C_{12}$) in the imidazolium systems is summarized in Table 2. This demonstrates that there is no advantage in the use of higher chain ionic liquids since, although the selectivity remains constant, the yield decreases steadily as chain length increases. One would expect that increasing the chain length would result in increased hydrogen solubility in the ionic liquid and this might, in turn, increase the conversion rate as the side chain lengthened. However, as the side chain lengthens, the ionic liquid becomes more viscous and mass transfer effects dominate the reaction, reducing the rate.

TABLE 2

Variation in hydrogenation of 1 using 5% Pt/graphite with increasing alkyl chain length in [$C_n$mim]+ ionic liquids.

| Solvent | % Conversion | % Selectivity 2 |
|---|---|---|
| bmimPF$_6$ | 43 | 84 |
| C$_6$mimPF$_6$ | 46 | 85 |
| C$_8$mimPF$_6$ | 35 | 83 |
| C$_{10}$mimPF$_6$ | 13 | 81 |
| *C$_{12}$mimPF$_6$ | 0 | 0 |

*ionic liquid is a solid at room temperature 1.5 Hydrogenation of Different Substrates in $C_6$mim NTf$_2$ with 5 wt % Pt/G A variety of different unsaturated aldehydes were reduced, so as to demonstrate that hydrogenations in ionic liquids are not restricted to the compounds reduced thus far.

The results for the reduction of four different compounds with 5 wt % Pt/G in $C_6$mim NTf$_2$ ionic liquid are shown in table 3.

TABLE 3

The reduction of four different substrates at 60° C. and 4 MPa after four hours with 5 wt % Pt/G in C$_6$mim NTf$_2$.

| Substrate | Product(s) | Amount |
|---|---|---|
| trans-2-octenal | (alcohol) | 100% |
| methyl vinyl ketone | (alcohol) | 100% |

TABLE 3-continued

The reduction of four different substrates at 60° C. and 4 MPa after four hours with 5 wt % Pt/G in $C_6$mim $NTf_2$.

| Substrate | Product(s) | Amount |
|---|---|---|
| 3-cyclohexene-1-carboxaldehyde | (saturated aldehyde) / (unsaturated alcohol) | 20% 56% |
| | (cyclohexene methanol) | |
| benzylidineacetone | (unsaturated alcohol) / (saturated ketone) | 20% <1% |

The results shown in Table 3 demonstrate that in the case of the substrates trans-2-octenal and methyl vinyl ketone, there was 100% formation of the fully saturated alcohol. For 3-cyclohexene-1-carboxaldehyde, 20% of the product was saturated aldehyde and for the reduction of benzylideneacetone the selectivity was found to be greater than 90% towards the alcohol product. It is worth noting that these reactions have not been optimised and therefore do not represent either the optimum in selectivity or activity in this or any other ionic liquid.

Example 2

2.0 Hydrogenation of Cinnamaldehyde in Ionic Liquids Using 10% Pd/activated carbon Palladium metal is known to reduce double bonds in preference to carbonyl groups, however, in α,β-unsaturated systems there is little or no selectivity in common organic solvents. Cinnamaldehyde hydrogenation carried out in propan-2-ol using Pd/activated carbon yielded the fully saturated compound, 3-phenylpropanol, 4.

Unless otherwise stated the reactions were performed under a hydrogen pressure of 4 MPa and a temperature of 60° C. The palladium catalysts were used as received. Ionic liquid (2 ml), 5.5 mg (10 wt % Pd catalyst), and cinnamaldehyde 0.5 ml (substrate/metal~800/1) were introduced to the autoclave and purged three times with argon. Hydrogen at $40 \times 10^5$ Pa was introduced and the autoclave heated to the required temperature. The reaction is left to stir for 6 h, upon which the reaction is cooled and the pressure released.

The reaction products were extracted using diethyl ether ($2 \times 10$ ml), which removes all the organic products whilst maintaining the catalyst in the ionic liquid. Product selectivities and conversions were determined using GC-FID.

Table 4 summarizes the results from reduction of cinnamaldehyde using Pd/C in a range of ionic liquids.

TABLE 4

Cinnamaldehyde hydrogenation variation with ionic liquid type using 10% wt Pd/activated carbon

| Ionic liquid | % 1 | % 3 | % 4 |
|---|---|---|---|
| bmimPF$_6$ | 0 | 100 | 0 |
| bmimBF$_4$ | 0 | 100 | 0 |
| C$_6$mimNTf$_2$ | 0 | 46 | 54 |
| emimNTf$_2$ | 0 | 38 | 62 |
| C$_6$pyBF$_4$ | 23 | 77 | 0 |
| C$_8$pyBF$_4$ | 42 | 46 | 12 |
| propan-2-ol | 0 | 0 | 100 |

It is clear from the table that the ionic liquid can adjust the selectivity towards hydrocinnamaldehyde, 3. Unlike in the case of platinum catalysts, all ionic liquid systems were found to be active, [PF$_6$]$^-$ and [BF$_4$]$^-$ systems gave high selectivity towards 3, in general, whereas [NTf$_2$]$^-$ gave a mixture of products. Under no conditions was cinnamyl alcohol produced using Pd/C.

2.1 Recycle.

Recycle of the palladium catalyst/ionic liquid was possible but as with the platinum case a reduction in conversion was observed on reuse. For example, recycle of Pd/C in bmimBF$_4$ showed 100% selectivity with conversion of 17%. Similar selectivities and conversions were observed for the 2nd, 3rd, 4th, 5th and 6th recycles. We believe that pore blocking may be the cause of the deactivation, at least in the case of activated carbon catalysts. Washing the catalyst with acetonitrile, prior to recycle after a first run had little effect on the conversion achieved. Increasing the catalyst loading from 800/1-100/1 increased the initial rate and all recycle (up to 5 recycles performed) showed 100% conversion and selectivity after 4 h to hydrocinnamaldehyde 3.

2.2 Effect of Pressure on Reaction Rates

FIG. 6 shows the variation of conversion after 4 h with hydrogen pressure. The pressure study showed that, even at low pressures such as $5\times10^5$ Pa there was significant conversion, after 4 h of the reaction. After 24 h, 93% conversion to hydrocinnamaldehyde 3 at $5\times10^5$ Pa was observed. At all pressures, only hydrocinnamaldehyde is found.

2.3 Temperature Study on the Effect of Conversion/Selectivity

The conversion of cinnamaldehyde increases with increasing temperature up to 60° C., whilst maintaining 100% selectivity to hydrocinnamaldehyde. Above 60° C., the selectivity decreases due to the hydrogenation of the carbonyl group, resulting in the formation of the fully saturated alcohol 4. There was no evidence for the formation of 4, when these reactions are run under standard conditions as described in the experimental procedure, even after prolonged reaction time (24 h).

TABLE 5

Cinnamaldehyde hydrogenation variation with temperature using 10% Pd/activated carbon.

| Temp (° C.) | % 1 | % 3 | % 4 | % selectivity 3 |
|---|---|---|---|---|
| 30 | 70 | 30 | 0 | 100 |
| 45 | 55 | 45 | 0 | 100 |
| 60 | 6 | 94 | 0 | 100 |
| 75 | 4 | 96 | 20 | 78 |
| 90 | 1 | 55 | 44 | 56 |

Example 3

3.0 Palladium Catalysed Hydrogenation of Methyl Oleate

The palladium catalysts were used as received. Ionic liquid (2 ml), 5.5 mg (10 wt % Pd catalyst), and methyl oleate 0.5 ml (substrate/metal~800/1) were introduced to the autoclave and purged three times with argon. Hydrogen at 1 MPa was introduced and the autoclave heated to the required temperature. The reaction is left to stir for 4 h, upon which the reaction is cooled and the pressure released.

The reaction products were extracted using diethyl ether (2×10 ml), which removes all the organic products whilst maintaining the catalyst in the ionic liquid. Product selectivities and conversions were determined using GC-FID.

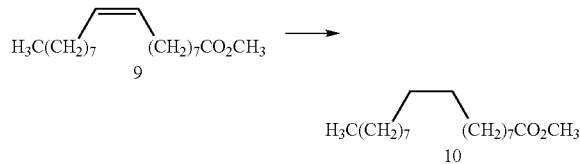

Methyl oleate 9 was hydrogenated to methyl stearate 10 with 100% conversion and selectivity after 4 h reaction at 60° C. in $C_6pyBF_4$, $bmimPF_6$ and $emimNTf_2$ ionic liquids. Following extraction the reaction was recycled and achieved the same conversions and selectivity. No cleavage of the ester group was observed and there was no loss of the catalyst to the extractant phase.

The so-formed product, 10, remains in the upper layer of the reaction mixture, i.e. above the ionic-liquid phase. Consequently, the product can be readily isolated by decantation, thus avoiding the need for extraction procedures. Thus, the use of ionic liquids in the hydrogenation of fatty acid esters may permit operation on a large scale by a continuous process. Additionally, it is noted that the hydrogenation reactions may be carried out in relatively small quantities of ionic liquid.

Example 4

4.0 Palladium Catalysed Hydrogenation of Citral

The palladium catalysts were used as received. Ionic liquid (2 ml), 5.5 mg (10 wt % Pd/C), and citral 0.5 ml (substrate/metal~800/1) were introduced to the autoclave and purged three times with argon. Hydrogen at 4 MPa was introduced and the autoclave heated to the required temperature. The reaction is left to stir for 6 h, upon which the reaction is cooled and the pressure released.

The reaction products were extracted using diethyl ether (2×10 ml), which removes all the organic products whilst maintaining the catalyst in the ionic liquid. Product selectivities and conversions were determined using GC-FID.

Citral has three sites of hydrogenation; the conjugate double bond, the carbonyl group and the isolated double bond. The hydrogenation of citral 11, a compound with a 'methyl blocking group', proceeded with selective hydrogenation of the double bond to produce citronellal 13. Literature reports had suggested that the selectivity in traditional solvents was governed by temperature.

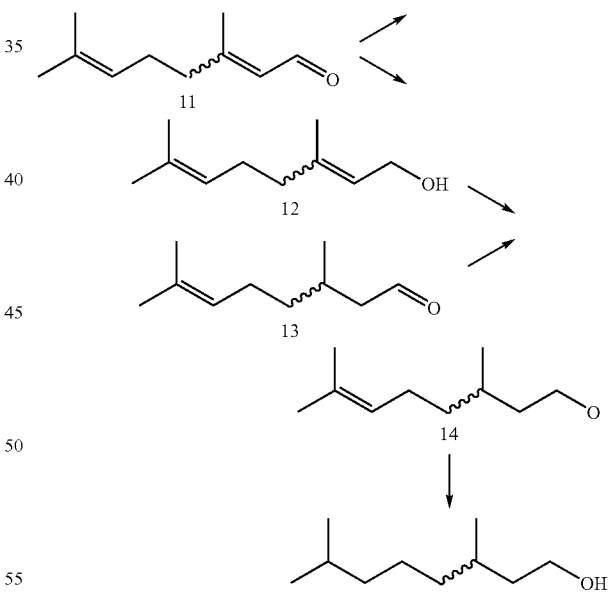

TABLE 6

Citral hydrogenation variation with ionic liquid type using 10 wt % Pd/C catalyst.

| Solvent | % Conversion | % Selectivity 2 |
|---|---|---|
| $emimNTf_2$ | 85 | 83 |
| $C_6mimNTf_2$ | 92 | 82 |

TABLE 6-continued

Citral hydrogenation variation with ionic liquid type using 10 wt % Pd/C catalyst.

| Solvent | % Conversion | % Selectivity 2 |
|---|---|---|
| $C_6mimPF_6$ | 72 | 96 |
| $bmimBF_4$ | 75 | 100 |
| $C_8PyBF_4$ | 56 | 100 |
| Propan-2-ol | 100 | 41 |

From Table 6, the results suggest that generally the $[BF_4]^-$ and the $[PF_6]^-$ ionic liquids are more selective than the $[NTf_2]^-$, however all ionic liquids tested are much more selective than propan-2-ol.

The temperature study produced conversion and selectivities analogous to those obtained using cinnamaldehyde 1 as the substrate. From 30° C.-60° C., the conversion increases whilst maintaining high selectivity. Above 60° C. the formation of the alcohol, citronellol 14, leads to a decrease in selectivity. The citral used for the experiment contains ~65% (E), 35% (Z) isomers. However, it is interesting to observe that the ratio of E/Z isomers of the unreacted citral in these experiments was still 65/35 indicating that the catalytic system did not discriminate between the isomers, even though ft was only selective for the reduction of the conjugated double bond. Even at high temperatures and pressures, were citronellol 14 was formed there was no evidence for the formation of the completely hydrogenated product 3,7-dimethyl octan-1-ol 15 or geraniol/nerol 12.

TABLE 7

Pd/C catalysed hydrogenation of citral at various temperatures in $bmimBF_4$

| Temp (° C.) | % 11 | % 13 | % 14 | E/Z ratio of unreacted 11 |
|---|---|---|---|---|
| 30 | 58 | 42 | 0 | 61/39 |
| 45 | 40 | 60 | 0 | 66/34 |
| 60 | 27 | 73 | 0 | 62/38 |
| 75 | 8 | 92 | 0 | 61/39 |
| 90 | 0 | 53 | 47 | 0 |

4.1 Modification of Heterogeneous Catalysts with Amino Acids

A series of palladium catalysts loaded onto to activated carbon, alumina and titania modified with (S)-proline (pro), (S)-phenylalanine (phal) and (S)-2-aminobutyric acid (aba) along with the alkaloid cinchonidine (cinc) were studied in the hydrogenation of citral.

Initial studies (Table 8) were carried out at 30° C. and 1 MPa on the palladium catalysts modified with proline according to the following procedure. The chiral modifier (0.01 mmol) was added to a suspension of ionic liquid 2 ml containing the palladium catalyst. The mixture was stirred for 1 h at 30° C. under 1 MPa of hydrogen to modify the catalyst surface before addition of the substrate molecule (0.52 ml of citral). The reaction was then re-pressurised to 1 MPa of $H_2$ and left to stir for 5 h, upon which the pressure is released.

The reaction products were extracted using organic solvent or distillation, which removes all the organic products whilst maintaining the catalyst in the ionic liquid. Product selectivities and conversions were determined using GC-FID.

TABLE 8

Heterogeneous hydrogenation[1] of citral over modified Pd

| Catalyst | Modifier | Solvent | Chemo-selectivity/% | Conversion/% |
|---|---|---|---|---|
| 10 wt % Pd/C | pro | Propan-2-ol | 33 | 89 |
| 10 wt % Pd/C | pro | cyclohexane | 57 | 85 |
| 10 wt % Pd/C | pro | $bmimBF_4$ | 88 | 73 |
| 10 wt % Pd/C[2] | pro | $bmimBF_4$ | 80 | 4 |
| 5 wt % Pd/Al$_2$O$_3$ | pro | $bmimBF_4$ | 100 | 49 |
| 5 wt % Pd/Al$_2$O$_3$[2] | pro | $bmimBF_4$ | 100 | 27 |
| 5 wt % Pd/TiO$_2$ | pro | $bmimBF_4$ | 100 | 31 |
| 5 wt % Pd/TiO$_2$[2] | pro | $bmimBF_4$ | 100 | 15 |
| 5 wt % Pd/TiO$_2$ | cinc | $bmimBF_4$ | 100 | 25 |
| 5 wt % Pd/TiO$_2$ | aba | $bmimBF_4$ | 100 | 18 |
| 5 wt % Pd/TiO$_2$ | phal | $bmimBF_4$ | 100 | 7 |

[1]Catalyst, modifier (0.01 mmol) and solvent (2 ml) combined and stirred for 1 hr at 30° C./1 MPa $H_2$; citral (0.52 ml) is added, S/C 600/1. Autoclave is filled up to 1 MPa $H_2$ and stirred for 5 h.
[2]Denotes recycle.

These results showed that citral is hydrogenated with excellent chemoselectivities in ionic liquid (Table 8). Furthermore, all of the catalysts give much higher chemoselectivities when employed in ionic liquid compared with propan-2-ol and cyclohexane.

An attempted recycle of the 10 wt % Pd/C/ $bmimBF_4$ system resulted in very poor conversion (4%) and a drop in chemoselectivity from 88% to 80%. Similar recycles of 5 wt % Pd/Al$_2$O$_3$ and 5 wt % Pd/TiO$_2$ in $bmimBF_4$ gave similar chemoselectivities as the initial run but the conversions decreased. The use of other chiral modifiers, such as phenylalanine, 2-aminobutyric acid and cinchonidine with 5 wt % Pd/TiO$_2$ in $bmimBF_4$ showed no advantage over the proline based system.

A kinetic study of the conversion and chemoselectivity of a 10 wt % Pd/C modified catalyst (proline) versus an unmodified catalyst shows that the reaction is faster in the modified system but the chemoselectivity drops with time (FIG. 7). The unmodified catalyst maintains 100% chemoselectivity throughout the reaction. The decrease in chemoselectivity observed with the modified catalyst is due to the over hydrogenation to citronellol.

Table 9 highlights the use of proline as a modifier on the reaction. (R)-proline, the unnatural enantiomer, as a chiral modifier again produces similar conversion and to chemoselectivity as the natural (S)-enantiomer. The use of cironellal as a promoter/modifier on recycle was not observed to increase chemoselectivity or conversion. Addition of fresh amounts of proline as well as the use of a proline saturated system shows excellent chemoselectivity and conversion on recycle.

TABLE 9

Effect of modifiers on catalyst recyclability

| Catalyst (5.5 mg) | Modifier (0.01 mmol) | Chemo-selectivity/% | Enantio-selectivity | Conversion/% |
|---|---|---|---|---|
| Pd/C | pro | 100 | 0 | 78 |
| Pd/C[1] | pro + pro[2] | 100 | 0 | 56 |
| Pd/C | sat. pro[5] | 100 | 0 | 73 |
| Pd/C[1] | sat. pro | 100 | 0 | 55 |
| Pd/C | pro | 98 | 0 | 42 |

TABLE 9-continued

Effect of modifiers on catalyst recyclability

| Catalyst (5.5 mg) | Modifier (0.01 mmol) | Chemo-selectivity/% | Enantio-selectivity | Conversion/% |
|---|---|---|---|---|
| Pd/C[1] | pro + cit[3] | 98 | 0 | 42 |
| Pd/C[4] | pro | 86 | 0 | 100 |
| Pd/C | (R)-pro[6] | 96 | 0 | 73 |

Standard reaction: 10 wt % Pd/C (5.5 mg), 5 wt % Pd/TiO$_2$ (11 mg), bmimBF$_4$ 2 ml, citral 0.52 ml. catalyst is modified at 30° C./1 MPa H$_2$ for 1 h, citral is injected and left to react for 5 h.
[1]Denotes recycle of above run.
[2]0.01 mmol proline added to original cycle and modified for 1 h.
[3]5% wt citronellal added to original cycle and modified for 1 h.
[4]Standard reaction system run overnight.
[5]Ionic liquid is saturated with (S)-proline before addition of 10 wt % Pd/C.
[6]Use of (R)-proline.

Table 10 shows the effect of a proline saturated ionic liquid on the recycle of 10 wt % Pd/C catalyst. The modified catalyst greatly increases the conversion upon the initial run and successive recycles while still maintaining 100% selectivity. Although the unmodified catalyst also shows 100% selectivity over the three recycles performed, the conversions upon recycle are much lower than modified catalyst.

TABLE 10

Catalyst recycle for 10 wt % Pd/C modified (sat. Proline) hydrogenation in bmim BF$_4$.

| | 10% Pd/C unmodified | | 10% Pd/C modified | |
|---|---|---|---|---|
| Run | % conversion | % selectivity | % conversion | % selectivity |
| 1 | 42 | 100 | 79 | 100 |
| 2 | 16 | 100 | 42 | 100 |
| 3 | 17 | 100 | 41 | 100 |
| 4 | 16 | 100 | 43 | 100 |

If a salt of proline is used, such a salt may remain suspended in the ionic liquid. Thus, separation of the product can easily be carried out by extraction procedures.

Example 5

Heterogeneously Catalysed Dehalogenation of 6-Chloropurine.

The palladium on carbon catalysts were used as received used whereas the platinum catalysts and palladium on alumina were pre-reduced in flowing hydrogen at 350° C. for 1 h. Ionic liquid (2 ml), 5.5 mg (10 wt % Pd on carbon), 11 mg (5 wt % palladium on alumina), 19.5 mg (5 wt % platinum on alumina), 19.5 mg (5 wt % platinum on graphite), and substrate (substrate/metal ~200/1) were introduced to the autoclave and purged three times with argon. Hydrogen at the desired pressure was introduced and the autoclave heated to the required temperature. The reaction is left to stir for the desired time period, upon which the reaction is cooled and the pressure released. The reaction products are extractable using water.

The reaction conversion and selectivity was analysed by HPLC.

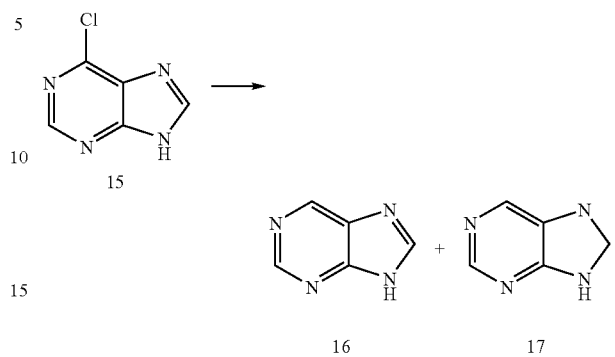

Table 11 shows the conversion and selectivity for the reaction to 16 over 17.

TABLE 11

Hydro-dehalogenation of 6-chloropurine[c] in bmim BF$_4$/PF$_6$

| Catalyst | Ionic liquid[b] | Pressure | Temperature | % Conversion[a] (Selectivity)[a] |
|---|---|---|---|---|
| 5 wt % Pt/G | bmimPF$_6$ | 10 | 60 | 59 (100) |
| 5 wt % Pt/G | bmimPF$_6$ | 40 | 60 | 82 (100) |
| 5 wt % Pt/Al$_2$O$_3$ | bmimBF$_4$ | 40 | 60 | 100 (83) |
| 5 wt % Pt/Al$_2$O$_3$ | bmimPF$_6$ | 40 | 60 | 100 (69) |
| 5 wt % Pd/Al$_2$O$_3$ | bmimBF$_4$ | 40 | 60 | 87 (100) |
| 5 wt % Pd/Al$_2$O$_3$ | bmimBF$_4$ | 10 | 60 | 76 (96) |
| 5 wt % Pd/Al$_2$O$_3$ | bmimPF$_6$ | 10 | 60 | 66 (92) |
| 5 wt % Pd/CaCO$_3$ | bmimBF$_4$ | 40 | 60 | 62 (98) |
| 5 wt % Pd/CaCO$_3$ | bmimBF$_4$ | 10 | 60 | 39 (99) |

[a]determined by HPLC, reaction monitored after 4 h
[b]ionic liquid volume 2 ml
[c]1 mmol of substrate added Pressure had little effect on selectivity for the platinum or palladium systems but lower pressure seemed to result in lower conversions. All of the catalysts used showed good conversion and good selectivity in the ionic liquids studied.

TABLE 12

Catalyst recycle for dechlorinations of 6-chloropurine in BmimBF$_4$

| | 5% Pd/Al$_2$O$_3$ | | 5% Pd/CaCO$_3$ | |
|---|---|---|---|---|
| Run | % conversion | % selectivity | % conversion | % selectivity |
| 1 | 94 | 100 | 67 | 100 |
| 2 | 38 | 98 | 62 | 95 |
| 3 | 30 | 97 | 60 | 99 |
| 4 | 23 | 99 | 51 | 100 |

Recycle of Pd/Al$_2$O$_3$ and Pd/CaCO$_3$ systems was conducted at 60° C. and 4 MPa of hydrogen S/C 200/1. Catalyst deactivation is thought to be a common problem through poisoning by HX, sintering or coking. Sintering of the catalyst is not thought to be an issue, as this has only been reported to occur in gas phase reactions. Table 12 shows that catalyst deactivation in ionic liquids is possibly due to hydrogen halide formation which is eliminated by the use of a basic support. The slight decrease in activity over the recycles may be due to coking.

The dehalogenation of a range of mono-substituted benzenes and substituted halofluorobenzenes is shown in Table 13. From Table 13 the selective dehalogenation of a range of substituted fluorobenzenes proceeds very smoothly producing only fluorobenzene. There is no spectral evidence for the defluorination to benzene or arene hydrogenation. Chlorobenzene proved to be more difficult to dehalogenate than bromobenzene but went to completion after 24 h, when $CaCO_3$ was used as the support. It has been well documented that side reactions such as dimerisation and hydroisomerisation can occur during the dehalogenation of chlorobenzene, although this has not been observed in our systems.

TABLE 13

Hydrogenation[a] of substituted benzenes in bmimBF$_4$

| Catalyst | Substrate | Conversion[b] |
|---|---|---|
| 5 wt % Pd/CaCO$_3$ | 4-Cl-fluorobenzene | 100%[c] |
| 5 wt % Pd/Al$_2$O$_3$ | 4-Cl-fluorobenzene | 100%[c] |
| 5 wt % Pd/CaCO$_3$ | 3-Cl-fluorobenzene | 100%[c] |
| 5 wt % Pd/CaCO$_3$ | 2-Cl-fluorobenzene | 100%[c] |
| 5 wt % Pd/CaCO$_3$ | 4-Br-fluorobenzene | 100%[c] |
| 5 wt % Pd/CaCO$_3$ | 3-Br-fluorobenzene | 100%[c] |
| 5 wt % Pd/CaCO$_3$ | 4-I-fluorobenzene | 100%[c] |
| 5 wt % Pd/Al$_2$O$_3$ | chlorobenzene | 2%[d] |
| 5 wt % Pd/CaCO$_3$ | chlorobenzene | 42%[d] |
| 5 wt % Pd/CaCO$_3$ | bromobenzene | 93%[d] |

[a]60 C, 4 MPa S/C 100:1, 4 h
[b]Monitored by GC
[c]conversion to fluorobenzene
[d]conversion to benzene Example 6

Heterogeneously Catalysed Reduction of Alkynes

The palladium catalysts were used as received. Ionic liquid (2 ml), 5.5 mg (5 wt % Pd on calcium carbonate, 10 wt % Pd on activated carbon, 5 wt % Pd/CaCO$_3$ lead poisoned), and substrate (substrate/metal ~800/1) were introduced to the autoclave and purged three times with argon. Hydrogen at the desired pressure was introduced and the autoclave heated to the required temperature. The reaction is left to stir for the desired time period, upon which the reaction is cooled and the pressure released.

The reaction products were extracted using organic solvent or distillation, which removes all the organic products whilst maintaining the catalyst in the ionic liquid. Product selectivities and conversions were determined using GC-FID.

Table 14 shows the conversion and selectivity for the reduction of 1-nonyne using 10% Pd/C and 5% Pd/CaCO$_3$ in a series of different alkyl chain length [Pyridinium]$^+$ [BF$_4$]$^-$ ionic liquids

TABLE 14

Reduction of 1-nonyne using 5 wt % Pd/CaCO$_3$ and 10 wt % Pd/C at 30° C. and 3 × 10$^5$ Pa for 4 hours.

| Catalyst & Ionic Liquid | Nonyne | Nonene | Nonane |
|---|---|---|---|
| 10 wt % Pd/C & C$_4$PyBF$_4$ | 0% | 0% | 100% |
| 10 wt % Pd/C & C$_6$PyBF$_4$ | 0% | 0% | 100% |
| 10 wt % Pd/C & C$_8$PyBF$_4$ | 0% | 0% | 100% |
| 5 wt % Pd/CaCO$_3$ & C$_4$PyBF$_4$ | 20% | 0% | 80% |
| 5 wt % Pd/CaCO$_3$ & C$_6$PyBF$_4$ | 45% | 55% | 0% |

Figure 8:
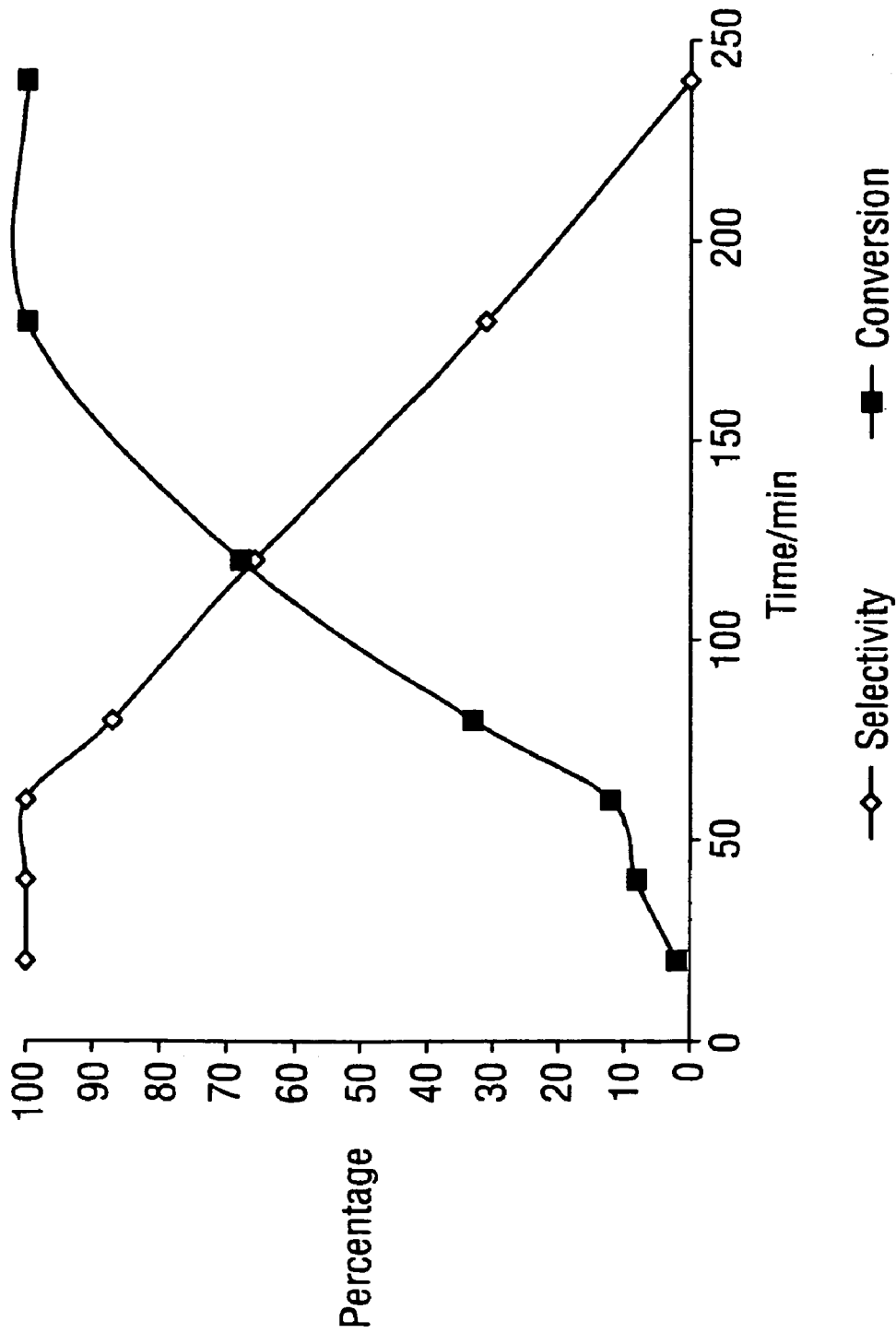

Table 14 shows that 10 wt % Pd/C gives complete reduction to the alkane after four hours. The kinetic graph in FIG. 8 shows that 10 wt % Pd/C is 100% selective, although only at low conversions. The 5 wt % Pd/CaCO$_3$/C$_6$PyBF$_4$ system, shows 100% selectivity towards the alkene up to at least 55% conversion, although the C$_4$ pyridinium BF$_4$ shows lower selectivity after 4 h under these reaction conditions. Table 15 shows the conversion and selectivity for the reduction of three different substrates using the 5 wt % Pd/CaCO$_3$/C$_6$PyBF$_4$ system.

TABLE 15

Reductions of different substrates using 5 wt % Pd/CaCO$_3$ at 30° C. & 3 × 10$^5$ Pa for 4 hrs.

| Catalyst and Ionic Liquid | Substrate | Conversion | Selectivity |
|---|---|---|---|
| 5 wt % Pd/CaCO$_3$ & C$_6$PyBF$_4$ | 1-nonyne | 55 | 100 |
| 5 wt % Pd/CaCO$_3$ & C$_6$PyBF$_4$ | 3-nonyn-1-ol | 11 | 100 |
| 5 wt % Pd/CaCO$_3$ & C$_6$PyBF$_4$ | Phenyl Acetylene | 75 | 94 |

Table 15 shows that high selectivity towards the alkene is achievable for all three substrates. The conversion and selectivity of phenyl acetylene towards styrene for a series of experiments varying the reaction pressure, temperature and length of reaction time are shown in FIGS. 9a, 9b and 9c.

The graphs of temperature and pressure shown in FIGS. 9a and 9b indicate that an increase in either the temperature or pressure has the effect of increasing the conversion but decreasing the selectivity.

FIG. 9c shows that when the reaction proceeds for longer than three hours, the selectivity drops off dramatically due to further hydrogenation to ethyl benzene, indicating that the only way to achieve maximum selectivity is to keep the reaction time and subsequently the level of conversion low. The inverse behaviour of the selectivity with respect to the conversion, explains why as of yet there are no conditions found where 100% conversion and 100% selectivity can be achieved.

Table 16 shows the reduction of phenyl acetylene in a range of ionic liquids using 5 wt % Pd/CaCO$_3$ poisoned with lead (Lindlars catalyst).

TABLE 16

Reductions of phenyl acetylene using Lindlars Catalyst at 30° C. and 5 × 10$^5$ Pa for 4 hours.

| Catalyst & Ionic Liquid | Phenyl Acetylene | Styrene | Ethyl Benzene |
|---|---|---|---|
| C$_{10}$mim BF$_4$ | 43% | 57% | 0% |
| C$_8$mim BF$_4$ | 45% | 55% | 0% |
| C$_6$Py NTf$_2$ | 75% | 25% | 0% |
| C$_8$mim NTf$_2$ | 17% | 83% | 0% |
| C$_6$mim NTf$_2$ | 3% | 97% | 0% |
| Bmim NTf$_2$ | 0% | 92% | 8% |

Lindlars catalyst maybe used in conjunction with range of ionic liquids to achieve at least 97% conversion with 100% selectivity for the reduction of phenyl acetylene to styrene.

CONCLUSION

Ionic liquids provide a medium for heterogeneously catalysed hydrogenations, which competes well with conventional solvents. Using unmodified carbon or oxide based platinum group metal catalysts, good selectivity to a range of products is achievable simply by selecting a particular ionic liquid. In these systems it is believed that the ionic liquid modifies the surface and allows the high selectivity to be achieved. Aside from the high selectivity, the use of ionic liquids for hydrogenation reactions provide other advantages over conventional solvents, such as the ease of extraction of the product molecule from the ionic liquid without the need to filter and reactivate the catalyst. This procedure leads to catalyst loss industrially and is a major safety hazard when used on a large scale. The ionic liquid based heterogeneous catalyst systems do deactivate significantly during the reaction compared with organic solvent systems. In these reactions, the ionic liquids cannot be treated as general solvents, as different ionic liquids promote different selectivities, which allows good control over the products without the need to change the catalyst.

The invention claimed is:

1. A process for the selective catalytic hydrogenation of a compound containing at least one unsaturated carbon-carbon bond and at least one other functional group, said process comprising reacting said compound with a hydrogenating agent and a heterogeneous hydrogenation catalyst in the presence of an ionic liquid, resulting in selective hydrogenation of the unsaturated carbon-carbon bond over the at least one other functional group.

2. A process according to claim 1 wherein the compound contains at least one C═C or C≡C bond.

3. A process according to claim 1 wherein the compound contains from 2 to 50 carbon atoms.

4. A process according to claim 1 wherein the compound includes a moiety selected from a group consisting of alkenes, alkynes, esters, ethers, carboxylic acids, amines, amides, alcohols, nitriles, aldehydes and ketones; or where the compound is selected from a group consisting of fatty acids and esters thereof, steroids, prostaglandins, isoprenoids, flavonoids icosanoids and compounds containing an aromatic moiety.

5. A process according to claim 1 wherein the compound has the formula:

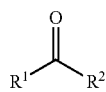

wherein:
$R^1$ is selected from a group consisting of hydrogen or $C_1$ to $C_{20}$ straight chain or branched alkyl or $C_3$ to $C_8$ cycloalkyl wherein said alkyl or cycloalkyl group may be substituted with 1-3 substituents independently selected from a group consisting of: $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, ═O, $C_1$ to $C_6$ alkylamino, $C_1$ to $C_6$ dialkylamino, —CN, $COOR^3$, $CONR^3$ or $OR^3$ wherein $R_3$ is selected from a group consisting of H, $C_1$ to $C_{20}$ alkyl and $C_6$ to $C_{10}$ aryl; or $C_6$ to $C_{10}$ aryl wherein said aryl group may be substituted with 1-3 substituents independently selected from a group consisting of $C_1$ to $C_{10}$ alkyl, hydroxyl, F, $CF_3$, CN, $COOR^4$, $CONR^4$ or $OR^4$ wherein $R^4$ is selected from a group consisting of H, $C_1$ to $C_{20}$ alkyl; and $R^2$ represents $C_1$ to $C_{20}$ straight chain or branched alkenyl or $C_5$ to $C_8$ cycloalkenyl wherein said alkenyl or cycloalkenyl group may be substituted with 1-3 substituents independently selected from a group consisting of $C_1$ to $C_{20}$ alkyl, $C_6$ to $C_{10}$ aryl, $C_8C_{20}$ aralkyl, $C_8$-$C_{20}$ alkaryl, $C_3$ to $C_8$ cycloalkyl, hydroxyl, F, $CF_3$, ═O, $C_1$ to $C_6$ alkylamino, $C_1$ to $C_6$ dialkylamino, —CN, $COOR^3$, $CONR^3$ or $OR^3$ wherein $R^3$ is selected from a group consisting of H, $C_1$ to $C_{20}$ alkyl and $C_6$ to $C_{10}$ aryl; or $C_6$ to $C_{10}$ aryl wherein said aryl group may be substituted with 1-3 substituents independently selected from a group consisting of $C_1$ to $C_{10}$ alkyl, hydroxyl, F, $CF_3$, CN, $COOR^4$, $CONR^4$ or $OR^4$ wherein $R^4$ is selected from a group consisting of H, $C_1$ to $C_1$ alkyl.

6. A process according to claim 1 wherein the compound has the formula:

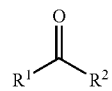

wherein:
$R^1$ is selected from a group consisting of hydrogen; $C_1$ to $C_{10}$ straight chain or branched alkyl; and $R^2$ represents $C_1$ to $C_{20}$ straight chain or branched alkenyl or $C_5$ to $C_8$ cycloalkenyl wherein said alkenyl or cycloalkenyl group may be substituted with 1-3 substituents independently selected from a group consisting of $C_1$ to $C_{20}$ alkyl or $C_6$ to $C_{10}$ aryl.

7. A process according to claim 1 wherein the compound comprises an α,β-unsaturated carbonyl moiety.

8. A process according to claim 1 wherein the compound is cinnamaldehyde, 2-octenal, methylvinylketone, 3-cyclohexene-1-carboxaldehyde and berizylidine acetone.

9. A process according to claim 1 wherein the compound has the formula:

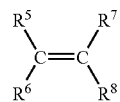

wherein:
$R^5$, $R^6$, $R^7$ and $R^8$ may be the same or different and each is independently selected from a group consisting of:
hydrogen;
$C_1$ to $C_{20}$ straight chain or branched alkyl or $C_3$ to $C_8$ cycloalkyl wherein said alkyl or cycloalkyl group may be substituted with 1-3 substituents independently selected from a group consisting of: $C_2$ to $C_{10}$ alkenyl, $C_5$ to $C_8$ cycloalkenyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, ═O, $C_1$ to $C_6$ alkylamino, $C_1$ to $C_6$ dialkylamino, —CN, $COOR^3$, $CONR^3$ or $OR^3$ wherein $R^3$ is selected from a group consisting of H, $C_1$ to $C_{20}$ alkyl and $C_6$ to $C_{10}$ aryl;
$C_2$ to $C_{20}$ straight chain or branched alkenyl;
$C_5$ to $C_8$ cycloalkenyl; or
$C_6$ to $C_{10}$ aryl wherein said aryl group may be substituted with 1-3 substituted independently selected from a group consisting of $C_1$ to $C_{10}$ alkyl, hydroxyl, F, $CF_3$, CN, $COOR^4$, $CONR^4$ or $OR^4$ wherein $R^4$ is selected from a group consisting of H and $C_1$ to $C_{20}$ alkyl.

10. A process according to claim 1 wherein the compound has the formula:

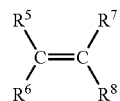

wherein $R^5$, $R^6$, $R^7$ and $R^8$ are the same or different and each is independently selected from a group consisting of:

hydrogen;

$C_1$ to $C_{20}$ straight chain or branched alkyl or $C_3$ to $C_8$ cycloalkyl; and $C_2$ to $C_{20}$ straight chain or branched alkenyl.

11. A process according to claim 10 wherein $R^5$ and $R^7$ each represents hydrogen.

12. A process according to claim 10 wherein $R^6$ and $R^8$ are each independently selected from a group consisting of $C_1$ to $C_{20}$ straight chain or branched alkyl, $C_3$ to $C_8$ cycloalkyl and $C_2$ to $C_{20}$ straight chain or branched alkenyl.

13. A process according to claim 1 wherein the compound has the formula:

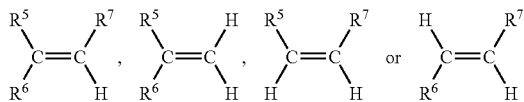

wherein $R^5$, $R^6$ and $R^7$ may be the same or different and each is independently selected from a group consisting of:

hydrogen;

$C_1$ to $C_{20}$ straight chain or branched alkyl or $C_3$ to $C_8$ cycloalkyl wherein said alkyl or cycloalkyl group may be substituted with 1-3 substituents independently to $C_6$ dialkylamino, —CN, $COOR^3$, $CONR^3$ or $OR^3$ wherein $R^3$ is selected from a group consisting of H, $C_1$ to $C_{20}$ alkyl and $C_6$ to $C_{10}$ aryl;

$C_2$ to $C_{20}$ straight chain or branched alkenyl;

$C_5$ to $C_8$ cycloalkenyl; or $C_6$ to $C_{10}$ aryl wherein said aryl group may be substituted with 1-3 substituted independently selected from a group consisting of $C_1$ to $C_{10}$ alkyl, hydroxyl, F, $CF_3$, CN, $COOR^4$, $CONR^4$ or $OR^4$ wherein $R^4$ is selected from a group consisting of H and $C_1$ to $C_{20}$ alkyl.

14. A process according to claim 1 wherein the compound has the formula:

wherein $R^9$ and $R^{10}$ are each independently selected from a group consisting of:

hydrogen;

$C_1$ to $0_{20}$ straight chain or branched alkyl or $C_3$ to $C_8$ cycloalkyl wherein said alkyl or cycloalkyl group may be substituted with 1-3 substituents independently selected from a group consisting of: $C_2$ to $C_{10}$ alkenyl, $C_5$ to $C_8$ cycloalkenyl, $C_6$ to $C_{10}$ aryl, $C_8$-$C_{20}$ aralkyl, $C_8$-$C_{20}$ alkaryl, $C_3$ to $C_8$ cycloalkyl, hydroxyl, F, $CF_3$, =0, $C_1$ to $C_6$ alkylamino, $C_1$ to $C_6$ dialkylamino, —CN, $COOR^3$, $CONR^3$ or $OR^3$ wherein $R^3$ is selected from a group consisting of H, $C_1$ to $C_{20}$ alkyl and $C_6$ to $C_{10}$ aryl; and $C_6$ to $C_{10}$ aryl wherein said aryl group may be substituted with 1-3 substituents independently selected from a group consisting of $C_1$ to $C_{10}$ alkyl, hydroxyl, F, $CF_3$, CN, $COOR^4$ $CONR^4$ or $OR^4$ wherein $R^4$ is selected from a group consisting of H and $C_1$, to $C_{20}$ alkyl.

15. A process according to claim 1 wherein: the compound has the formula $R^9C\!\!=\!\!CR^{10}$ wherein $R^9$ and $R^{10}$ are each independently selected from a group consisting of:

hydrogen;

$C_1$ to $C_{20}$ straight chain or branched alkyl or $C_3$ to $C_8$ cycloalkyl; and $C_6$ to $C_{10}$ aryl wherein said aryl group may be substituted with 1-3 substituents independently selected from a group consisting of $C_1$ to $C_{10}$ alkyl, hydroxyl, F or $OR^4$ wherein $R^4$ is selected from a group consisting of H and $C_1$ to $C_{20}$ alkyl.

16. A process according to claim 1 wherein the ionic liquid is an imidazolium, pyridinium, pyridazinium, pyrazinium, oxazolium, triazolium or pyrazolium salt.

17. A process according to claim 1 wherein the ionic liquid is a salt of an alkylated or polyalkylated compound of pyridine, pyridazine, pyrimidine, pyrazine, imidazole, pyrazole, oxazole or triazole.

18. A process according to claim 1 wherein the ionic liquid has the formula:

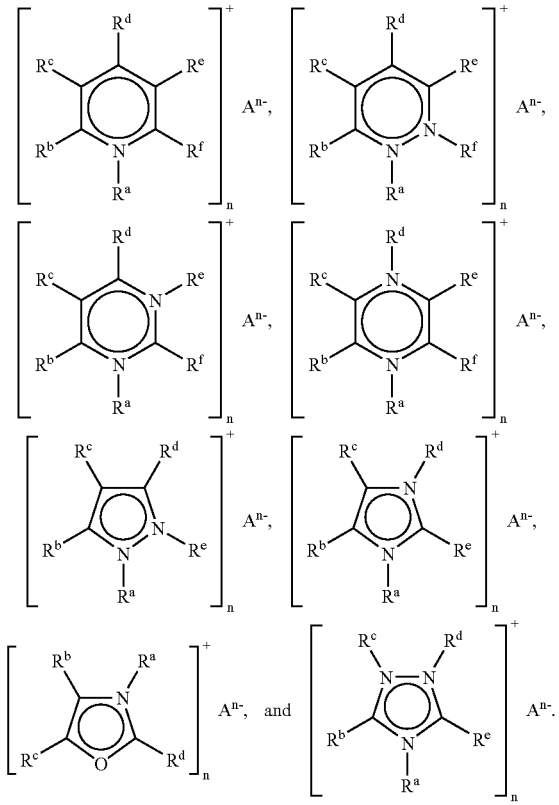

wherein $R^a$ is a $C_1$ to $C_{40}$ straight chain or branched alkyl or $C_3$ to $C_8$ cycloalkyl group, wherein said alkyl or cycloalkyl group which may be substituted by one to three groups selected from a group consisting of: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl; $R^b$, $R^c$, $R^d$, $R^e$ and $R^f$ can be the same or different and are each independently selected from a group consisting of H or any of the $R^a$ groups as defined above; and A represents an anion having a charge n–; wherein n may be 1-3.

19. A process according to claim 18 wherein $R^a$ represents $C_4$ to $C_{12}$ straight chain or branched alkyl.

20. A process according to claim 18 wherein $R^b$, $R^c$, $R^d$, $R^e$ and $R^f$ are hydrogen.

21. A process according to claim 1 wherein the ionic liquid has the formula:

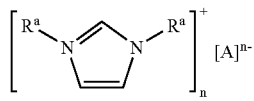

wherein
each $R^a$ may be the same or different and each is independently selected from a group consisting of $C_1$ to $C_{40}$ straight chain or branched alkyl which may be substituted by one to three groups selected from a group consisting of: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;
A represents one or more species of anion having valency n; and
n represents 1-3.

22. A process according to claim 1 wherein the ionic liquid has the formula:

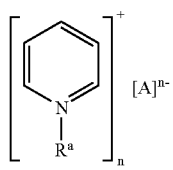

wherein
$R^a$ is selected from a group consisting of $C_1$ to $C_{40}$ straight chain or branched alkyl which may be substituted by one to three groups selected from a group consisting of: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;
A represents one or more species of anion having valency n;
and n represents 1-3.

23. A process according to claim 18 wherein $R^a$ is independently selected from a group consisting of $C_1$ to $C_{40}$ straight chain or branched alkyl.

24. A process according to claim 18 wherein each $R^a$ and $R^b$ is independently selected from a group consisting of $C_4$ to $C_{12}$ straight chain or branched alkyl.

25. A process according to claim 18 wherein A represents a single species of anion having valency n.

26. A process according to claim 18 wherein n is 1.

27. A process according to claim 9 wherein A represents an anion selected from a group consisting of boron or phosphorus fluorides, $NO_3$, $SO_4$, $HSO_4$, $HCO_3$, $[(CF_3SO_2)_2N]$, $[AsF_6]$, alkylsulfonates, mono- or difluorinated alkyl sulfonates including perfluorinated alkylsulfonates, carboxylic acid anions, fluorinated carboxyic acid anions and metal halides.

28. A process according to claim 18 wherein A represents an anion selected from a group consisting of $[PF_6]$, $[BF_4]$ and $[(CF_3SO_2)_2N]$.

29. A process according to claim 1 wherein the heterogeneous hydrogenation catalyst comprises nickel, palladium, ruthenium, iridium, rhodium and platinum.

30. A process according to claim 1 wherein the catalyst is supported on an inert support.

31. A process according to claim 1 wherein the catalyst is supported on an inert support wherein said inert support comprises activated carbon, alumina, silica, silica-alumina, carbon black, graphite, titania, zirconia, calcium carbonate, and barium sulfate.

32. A process according to claim 1 wherein the particle size of the heterogeneous hydrogenation catalyst is up to 200 A.

33. A process according to claim 1 wherein the catalyst particle size, including support (if any) is selected from the group consisting of greater than 20 μm, greater than 50 μm, and greater than 100 μm.

34. A process according to claim 1 wherein the hydrogenating agent is molecular hydrogen, molecular deuterium, HD, molecular tritium, HT, DT, or an organic or inorganic hydrogen, deuterium or tritium transfer agent.

35. A process according to claim 1 wherein the hydrogenating agent is molecular hydrogen.

* * * * *

UNITED STATES PATENT AND TRADEMARK OFFICE
CERTIFICATE OF CORRECTION

PATENT NO. : 7,667,058 B2 Page 1 of 1
APPLICATION NO. : 10/478039
DATED : February 23, 2010
INVENTOR(S) : Anderson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Twenty-eighth Day of December, 2010

David J. Kappos
*Director of the United States Patent and Trademark Office*